(12) United States Patent
Yachida

(10) Patent No.: US 11,776,312 B2
(45) Date of Patent: Oct. 3, 2023

(54) IMAGE PROCESSING DEVICE, IMAGE PROCESSING METHOD, AND STORAGE MEDIUM

(71) Applicant: NEC Corporation, Tokyo (JP)

(72) Inventor: Shoji Yachida, Tokyo (JP)

(73) Assignee: NEC CORPORATION, Tokyo (JP)

(*) Notice: Subject to any disclaimer, the term of this patent is extended or adjusted under 35 U.S.C. 154(b) by 0 days.

(21) Appl. No.: 17/680,875

(22) Filed: Feb. 25, 2022

(65) Prior Publication Data

US 2022/0180656 A1 Jun. 9, 2022

Related U.S. Application Data

(63) Continuation of application No. 17/312,614, filed as application No. PCT/JP2018/046446 on Dec. 18, 2018.

(51) Int. Cl.
*G06V 40/00* (2022.01)
*G06V 40/16* (2022.01)
(Continued)

(52) U.S. Cl.
CPC ............ *G06V 40/171* (2022.01); *G06V 10/50* (2022.01); *G06V 10/803* (2022.01);
(Continued)

(58) Field of Classification Search
CPC .... G06V 40/171; G06V 10/50; G06V 10/803; G06V 40/166; G06V 40/19;
(Continued)

(56) References Cited

U.S. PATENT DOCUMENTS 5,598,145 A 1/1997 Shimotani et al.
2011/0228975 A1* 9/2011 Hennessey ............. G06F 3/013
382/103
(Continued)

FOREIGN PATENT DOCUMENTS

JP H03-165737 A 7/1991
JP H07134800 A 5/1995
(Continued)

OTHER PUBLICATIONS

JP Office Action for JP Application No. 2020-560667, dated Jul. 26, 2022 with English Translation.
(Continued)

*Primary Examiner* — Md K Talukder

(57) ABSTRACT

An image processing device according to one aspect of the present disclosure includes: at least one memory storing a set of instructions; and at least one processor configured to execute the set of instructions to: receive a visible image of a face; receive a near-infrared image of the face; adjust brightness of the visible image based on a frequency distribution of pixel values of the visible image and a frequency distribution of pixel values of the near-infrared image; specify a relative position at which the visible image is related to the near-infrared image; invert adjusted brightness of the visible image; detect a region of a pupil from a synthetic image obtained by adding up the visible image the brightness of which is inverted and the near-infrared image based on the relative position; and output information on the detected pupil.

17 Claims, 17 Drawing Sheets

(51) Int. Cl.
*G06V 40/19* (2022.01)
*G06V 10/80* (2022.01)
*G06V 10/50* (2022.01)
*G06V 40/18* (2022.01)

(52) U.S. Cl.
CPC ............ *G06V 40/166* (2022.01); *G06V 40/19* (2022.01); *G06V 40/193* (2022.01)

(58) Field of Classification Search
CPC .. G06V 40/193; A61B 3/0025; A61B 5/0077; A61B 5/1176; G06F 18/251
See application file for complete search history.

(56) References Cited

U.S. PATENT DOCUMENTS

| | | | |
|---|---|---|---|
| 2014/0099005 A1 | 4/2014 | Mogi | |
| 2016/0011657 A1* | 1/2016 | Estacio | G06V 40/193 345/156 |
| 2017/0039411 A1 | 2/2017 | Ono | |
| 2018/0032815 A1 | 2/2018 | Lee et al. | |
| 2018/0140187 A1* | 5/2018 | Watanabe | G06V 40/19 |
| 2018/0330160 A1* | 11/2018 | Yamamoto | H04N 23/611 |
| 2019/0387150 A1* | 12/2019 | Iwakura | H04N 23/45 |
| 2021/0365672 A1* | 11/2021 | Hu | G06V 40/193 |
| 2022/0036046 A1* | 2/2022 | Yachida | G06V 10/803 |
| 2022/0180656 A1* | 6/2022 | Yachida | G06F 18/251 |

FOREIGN PATENT DOCUMENTS

| | | | |
|---|---|---|---|
| JP | 2001340300 A | | 12/2001 |
| JP | 2008-246004 A | * | 10/2008 |
| JP | 2008246004 A | | 10/2008 |
| JP | 4528980 B2 | | 8/2010 |
| JP | 2014-078052 A | | 5/2014 |
| JP | 2015232771 A | | 12/2015 |
| JP | 2016093253 A | | 5/2016 |
| JP | 2016095584 A | | 5/2016 |
| JP | 2017038162 A | | 2/2017 |

OTHER PUBLICATIONS

International Search Report for PCT Application No. PCT/JP2018/046446, dated Mar. 19, 2019.
English translation of Written opinion for PCT Application No. PCT/JP2018/046446, dated Mar. 19, 2019.
Extended European Search Report for EP Application No. 18943419.4 dated Mar. 14, 2022.
Bodade Rajesh et al:, "Chapter 3.4.4 Pupil Detection", Iris Analysis for Biometric Recognition Systems, Springer, Feb. 2, 2014.
Koschan Andreas et al:, "Chapter 12.4.6 Experimental Results", Digital Color Image Processing, John Wiley & Sons, Feb. 2, 2008.
U.S. Office Action for U.S. Appl. No. 17/312,614, dated Jan. 31, 2023.
U.S. Office Action for U.S. Appl. No. 17/680,869 dated Feb. 8, 2023.

* cited by examiner

IMAGE PROCESSING DEVICE, IMAGE PROCESSING METHOD, AND STORAGE MEDIUM

The present application is a Continuation application of Ser. No. 17/312,614 filed on Jun. 10, 2021, which is a National Stage Entry of PCT/JP2018/046446 filed on Dec. 18, 2018, the contents of all of which are incorporated herein by reference, in their entirety.

TECHNICAL FIELD

The disclosure relates to a technology of processing an image, and especially relates to a technology related to detection of a pupil from an image.

BACKGROUND ART

For example, at a walk-through gate at which a camera is installed, in a case where authentication is performed using an image of a site (for example, an iris or a face) of a body of a person to be authenticated imaged by the camera without stopping the person to be authenticated, it is necessary to quickly specify a position of the site in the image. In a case where the iris or the face is used as the site to be authenticated, if the position of a pupil may be quickly detected, the position of the iris or the face may be quickly specified based on the position of the pupil. A human pupil has a retroreflection characteristic with respect to near-infrared light (for example, an electromagnetic wave having a wavelength around 850 nanometer (nm)). PTL 1 discloses a pupil detection device that detects a pupil based on a difference in brightness of the pupil from a difference image of two images of a subject irradiated with light of two different wavelengths (for example, 850 nm and 950 nm) across 900 nm.

CITATION LIST

Patent Literature

[PTL 1] Japanese Patent No. 4528980

SUMMARY OF INVENTION

Technical Problem

In the technology disclosed in PTL 1, it is required that optical axes of two light sources having different wavelengths of emitted light and optical axes of two imaging devices that selectively receive the light of the wavelengths be common. Therefore, it is required to adjust installation positions of the two light sources, the two imaging devices, and a device such as a half mirror, for example, that changes an optical path so that the optical axes of the light sources and the imaging devices are common. Furthermore, it is required to correctly adjust a light emission timing of the light source and an imaging timing so that the imaging device that receives the light of the wavelength emitted by the light-emitting light source performs imaging while the light source emits light. In order to cause the two light sources to simultaneously emit light and simultaneously obtain two images irradiated with light of the two wavelengths, respectively, a device that separates light into light of a wavelength longer than about 900 nm and light of a wavelength shorter than about 900 nm is required. Such a device may be a dichroic mirror that separates light into light of a wavelength longer than about 900 nm and light of a wavelength shorter than about 900 nm. Such a device may be a combination of a low-pass filter and a high-pass filter, each of which has a cutoff wavelength of about 900 nm.

Therefore, in the technology of PTL 1, in order to detect the pupil from the image, the two light sources, the device that separates near-infrared light at a specific wavelength and the like are required in addition to the device that captures the image. Furthermore, it is necessary to correctly arrange the two light sources and the device such as the half mirror in addition to the two imaging devices. That is, the technology of PTL 1 requires a cost of these devices and a cost of correctly installing these devices.

An object of the disclosure is to provide an image processing device that reduces a cost for detecting a pupil.

Solution to Problem

An image processing device according to one aspect of the disclosure includes a first input means for receiving a visible image of a face, a second input means for receiving a near-infrared image of the face, an adjustment means for adjusting brightness of the visible image based on a frequency distribution of pixel values of the visible image and a frequency distribution of pixel values of the near-infrared image, an alignment means for specifying a relative position at which the visible image is related to the near-infrared image, an inversion means for inverting adjusted brightness of the visible image, a pupil detection means for detecting a region of a pupil from a synthetic image obtained by adding up the visible image the brightness of which is inverted and the near-infrared image based on the relative position, and an output means for outputting information on the detected pupil.

An image processing method according to one aspect of the disclosure includes receiving a visible image of a face, receiving a near-infrared image of the face, adjusting brightness of the visible image based on a frequency distribution of pixel values of the visible image and a frequency distribution of pixel values of the near-infrared image, an alignment means for specifying a relative position at which the visible image is related to the near-infrared image, inverting adjusted brightness of the visible image, detecting a region of a pupil from a synthetic image obtained by adding up the visible image the brightness of which is inverted and the near-infrared image based on the relative position, and outputting information on the detected pupil.

A storage medium according to one aspect of the disclosure stores a program that causes a computer to execute first input processing for receiving a visible image of a face, second input processing for receiving a near-infrared image of the face, adjustment processing for adjusting brightness of the visible image based on a frequency distribution of pixel values of the visible image and a frequency distribution of pixel values of the near-infrared image, alignment processing for specifying a relative position at which the visible image is related to the near-infrared image, inversion processing for inverting adjusted brightness of the visible image, pupil detection processing for detecting a region of a pupil from a synthetic image obtained by adding up the visible image the brightness of which is inverted and the near-infrared image based on the relative position, and output processing for outputting information on the detected pupil.

EXAMPLE EMBODIMENT

Next, example embodiments of the disclosure are described in detail with reference to the drawings.

First Example Embodiment

First, a configuration of an image processing device according to a first example embodiment is described, and next, an operation of the image processing device according to the first example embodiment is described.

Configuration

Figure 1:
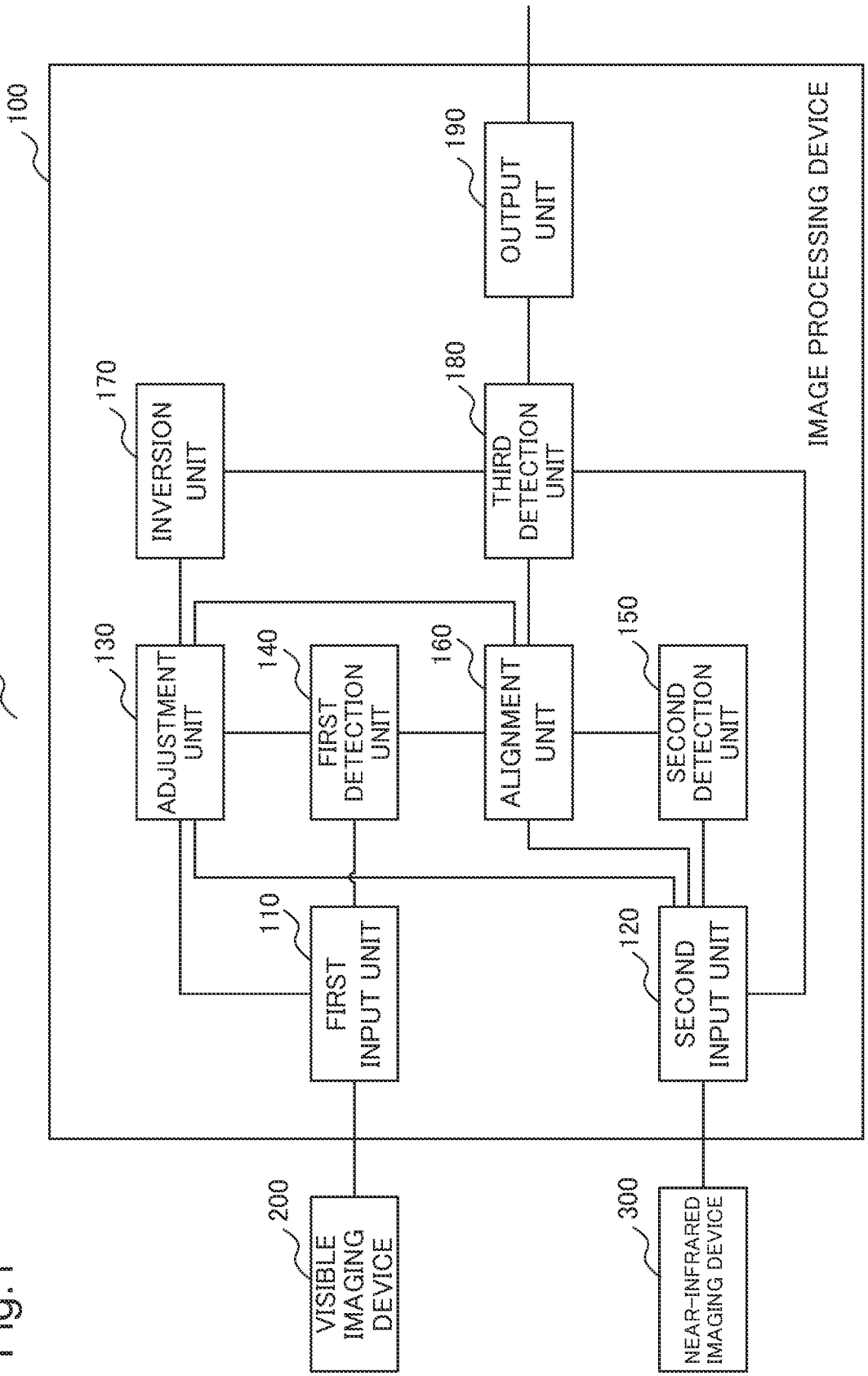
FIG. 1 is a block diagram illustrating an example of a configuration of an image processing system according to a first example embodiment of the disclosure.

FIG. 1 is a block diagram illustrating an example of a configuration of an image processing system 1 according to the first example embodiment. The image processing system 1 includes an image processing device 100, a visible imaging device 200, and a near-infrared imaging device 300.

The image processing device 100 illustrated in FIG. 1 includes a first input unit 110, a second input unit 120, an adjustment unit 130, a first detection unit 140, a second detection unit 150, an alignment unit 160, an inversion unit 170, a third detection unit 180, and an output unit 190. The visible imaging device 200 and the near-infrared imaging device 300 are connected to the image processing device 100.

The visible imaging device 200 is an imaging device that performs imaging in a visible light wavelength range. The visible imaging device 200 is achieved by, for example, a video camera or a digital camera. The visible imaging device 200 outputs a captured image. The image output by the visible imaging device 200 may be a color image. The image output by the visible imaging device 200 may be a grayscale image. A format of the image is any of formats decodable by the image processing device 100.

The near-infrared imaging device 300 is an imaging device that performs imaging in a near-infrared wavelength range in which a human retina has a retroreflection characteristic. The near-infrared imaging device 300 is achieved by an infrared camera capable of imaging near-infrared light in a wavelength range (for example, a wavelength range including a wavelength of 850 nm) in which the human retina has the retroreflection characteristic. The near-infrared imaging device 300 outputs a captured image. The image output by the near-infrared imaging device 300 is, for example, a grayscale image. A format of the image may be any of formats decodable by the image processing device 100.

The visible imaging device 200 and the near-infrared imaging device 300 are installed so as to be able to image the same target. The visible imaging device 200 and the near-infrared imaging device 300 may be installed adjacent to each other, for example. The visible imaging device 200 and the near-infrared imaging device 300 may be installed so that optical axes thereof are oriented in similar directions. The optical axis of the visible imaging device 200 is not required to be the same as the optical axis of the near-infrared imaging device 300. The visible imaging device 200 and the near-infrared imaging device 300 may be installed, for example, at a gate such as a walk-through gate, beside a door and the like. For example, the visible imaging device 200 and the near-infrared imaging device 300 may be configured to image a person (for example, a face of the person) passing through the gate and the like at which the visible imaging device 200 and the near-infrared imaging device 300 are installed at similar timings. It is not required that an angle of view and the number of pixels of the visible imaging device 200 be the same as those of the near-infrared imaging device 300.

Hereinafter, a case where the visible imaging device 200 and the near-infrared imaging device 300 image the face of the same person at the same timing is described.

The image processing device 100 is connected to the visible imaging device 200 in a wireless manner, a wired manner, or a combination of them so that the image processing device 100 may receive the image captured by the visible imaging device 200. Similarly, the image processing device 100 is connected to the near-infrared imaging device 300 in a wireless manner, a wired manner, or a combination of them so that the image processing device 100 may receive the image captured by the near-infrared imaging device 300.

The first input unit 110 receives the image captured by the visible imaging device 200 from the visible imaging device 200. In a case where the visible imaging device 200 outputs the color image, the first input unit 110 converts the received color image into a grayscale image. A method of converting the color image into the grayscale image may be any of existing methods according to a color space of a pixel value of each pixel. For example, in a case where the pixel value of one pixel is represented by contrast values of three colors of red, green, and blue, the method of converting may be setting a value obtained by applying a predetermined weight to each of the contrast values of the three colors of the pixel value and adding them up for each pixel of the color image as a pixel value of the grayscale image. In a case where the pixel value of the color image contains brightness as a component, the brightness may be set as the pixel value of the grayscale image. In the following description, the grayscale image output by the visible imaging device 200 and received by the first input unit 110 and the grayscale image converted from the color image output by the visible imaging device 200 and received by the first input unit 110 are expressed as visible input images. The visible input image is sometimes also expressed as a visible image. The first input unit 110 transmits the visible input image to the adjustment unit 130. The first input unit 110 may transmit the visible input image to the first detection unit 140.

The second input unit 120 receives the image captured by the near-infrared imaging device 300 from the near-infrared imaging device 300. In the following description, the image output by the near-infrared imaging device 300 and received by the second input unit 120 is expressed as a near-infrared input image. The near-infrared input image is sometimes also expressed as a near-infrared image. The second input unit 120 transmits the received near-infrared input image to the adjustment unit 130 and the second detection unit 150. The second input unit 120 may transmit the received near-infrared input image to the third detection unit 180.

The adjustment unit 130 receives the visible input image from the first input unit. The adjustment unit 130 further receives the near-infrared input image from the second input unit 120. The adjustment unit 130 matches a level of brightness of the visible input image to a level of brightness of the near-infrared input image based on a frequency distribution (that is, a histogram) of the pixel values (that is, brightness) of the visible input image and a frequency distribution of the pixel values of the near-infrared input image. The adjustment unit 130 adjusts the pixel values of the visible input image so that the histogram of the visible input image approaches the histogram of the near-infrared input image, for example, as follows.

Specifically, the adjustment unit 130 first generates the histogram of the visible input image and the histogram of the near-infrared input image. The number and width of bins of the histogram may be appropriately determined. The adjustment unit 130 further detects a peak of a dark portion in the histogram of the visible input image and the histogram of the near-infrared input image. The peak of the dark portion may be, for example, a bin representing a frequency of the darkest pixel value among the bins in which the frequency satisfies a predetermined criterion in magnitude, the bins representing the peak (that is, a maximum value of the frequency) of the histogram. The predetermined criterion described above may be, for example, exceeding multiplication by an appropriately determined constant less than one of a mode value. The peak of the dark portion is not limited to this example. For example, this may be the pixel value represented by the bin of the highest frequency out of the peak in a predetermined range from the bin related to the darkest pixel value. The pixel value represented by the bin may be a representative value (for example, an average, a maximum value, a minimum value or the like) of a range of the pixel values related to the bin. In the following description, the pixel value representing the peak of the dark portion of the histogram (that is, the pixel value represented by the bin of the peak of the dark portion of the histogram) is expressed as a dark portion peak pixel value.

The adjustment unit 130 first calculates a value (hereinafter, expressed as a dark portion offset value) obtained by subtracting the dark portion peak pixel value of the visible input image from the dark portion peak pixel value of the near-infrared input image. The calculated dark portion offset value is added to the pixel value of each pixel of the visible input image so that the peak of the dark portion of the histogram of the visible input image coincides with the peak of the dark portion of the histogram of the near-infrared input image.

The adjustment unit 130 may further adjust the pixel values of the visible input image so that the histogram of the pixel values of the visible input image in a range excluding a range including the peak of the dark portion is the closest to the histogram of the pixel values of the near-infrared input image, for example. The range including the peak of the dark portion described above may be, for example, a range including the bin of the peak of the dark portion, the range in which the bins of the frequency higher than a value obtained by multiplying a predetermined constant by the frequency of the peak of the dark portion are continuous. The predetermined constant may be appropriately determined. In the following description, out of the range of the bins with which the frequency distribution is represented by the histogram, a range not excluded as the range including the peak of the dark portion is expressed as a target range.

For example, the adjustment unit 130 may adjust the pixel values of the visible input image by multiplying adjustment magnification by a difference between the pixel value of each pixel of the visible input image in a state in which the dark portion offset value is added to the pixel value of each pixel and the dark portion peak pixel value. In other words, to adjust the pixel values of the visible input image in this case is to change the pixel value of each pixel of the visible input image to the sum of the dark portion peak pixel value and a value obtained by multiplying the adjustment magnification by a value obtained by subtracting the dark portion peak pixel value from the pixel value. For example, the adjustment unit 130 may calculate an adjustment value with which the histogram of the visible input image in a case where the pixel values of the visible input image are adjusted coincides the most with the histogram of the near-infrared input image.

The adjustment unit 130 may calculate the adjustment magnification at which the frequency distribution of the target range in the histogram of the visible input image in a case where the adjustment is performed is the closest to the distribution of the target range in the histogram of the near-infrared input image. Specifically, for example, the adjustment unit 130 may calculate an average of absolute values of differences in frequency of related bins in a common range between the target range of the histogram of the adjusted visible input image and the target range of the histogram of the near-infrared input image as a value representing proximity of the distribution. Then, the adjustment unit 130 may specify the adjustment magnification at which the value representing the proximity of the distribution is the smallest. The adjustment unit 130 makes the adjusted visible input image in a case where the adjustment magnification is the specified adjustment magnification the visible input image (hereinafter, expressed as an adjusted visible image) in which the pixel values are adjusted so that the histogram approaches the histogram of the near-infrared input image.

In a case where the pixel value of the pixel of the adjusted visible image becomes smaller than a possible minimum value as the pixel value, the adjustment unit 130 changes the pixel value of the pixel to the possible minimum value as the pixel value. In a case where the pixel value of the pixel of the adjusted visible image becomes larger than a possible maximum value as the pixel value, the adjustment unit 130 changes the pixel value of the pixel to the possible maximum value as the pixel value. The possible minimum value as the pixel value may be, for example, the minimum value (that is, a lower limit) of the pixel value in a value range of the pixel values of the visible input image. The possible maximum value as the pixel value may be, for example, the maximum value (that is, an upper limit) of the pixel value in the value range of the pixel values of the visible input image. Even in a case where the pixel value of the pixel of the adjusted visible image is not included in the value range of the pixel values of the visible input image, the adjustment unit 130 does not have to change the pixel value of the pixel to the upper limit or the lower limit of the value range of the pixel values.

The adjustment unit 130 may further detect a peak of a bright portion of the histogram of the near-infrared input image. The peak of the bright portion may be, for example, for example, a bin representing a frequency of the brightest pixel value among the bins in which the frequency satisfies a predetermined criterion in magnitude, the bins representing the peak (that is, a maximum value of the frequency) of the histogram. The peak of the bright portion may be, for example, a bin representing a frequency of the brightest pixel value among the bins in which the frequency satisfies a predetermined criterion in magnitude, the bins representing the peak (that is, a maximum value of the frequency) of the histogram. The predetermined criterion described above may be, for example, exceeding multiplication by an appropriately determined constant less than one of a mode value. The peak of the bright portion is not limited to this example. For example, this may be the pixel value represented by the bin of the highest frequency out of the peak in a predetermined range from the bin related to the brightest pixel value. The pixel value represented by the bin may be a representative value (for example, an average, a maximum value, a minimum value or the like) of a range of the pixel values related to the bin.

Then, the adjustment unit 130 may exclude a range including the peak of the bright portion from the target range of the near-infrared input image. The range including the peak of the bright portion excluded from the target range may be, for example, a range including the bin of the peak of the bright portion, the range in which the bins of the frequency higher than a value obtained by multiplying a predetermined constant by the frequency of the peak of the bright portion are continuous. The predetermined constant may be appropriately determined.

The adjustment unit 130 may further detect the peak of the bright portion of the histogram of the visible input image by a method similar to that in a case of detecting the peak of the bright portion of the histogram of the near-infrared input image. A predetermined criterion in a case of detecting the peak of the bright portion of the histogram of the visible input image may be different from the predetermined criterion in a case of detecting the peak of the bright portion of the histogram of the near-infrared input image.

In a case where the peak of the bright portion of the histogram of the visible input image is detected, a range including the peak of the bright portion may be excluded from the target range of the visible input image. The range including the peak of the bright portion of the visible input image may be defined similarly to the range including the peak of the bright portion of the near-infrared input image. In a case where the peak of the bright portion of the histogram of the visible input image is not detected, the adjustment unit 130 does not perform processing for excluding the range including the peak of the bright portion of the visible input image from the target range.

In a case where the range including the peak of the bright portion is excluded from the target range in at least one of the near-infrared input image and the visible input image, the adjustment unit 130 adjusts the visible input image based on the target range from which the range including the peak of the bright portion is excluded.

The first detection unit 140 receives the visible input image from the first input unit 110. The first detection unit 140 detects a face from the received visible image. A method by which the first detection unit 140 detects the face from the visible input image may be any of various existing methods. In a case where no face is detected from the visible input image, the image processing device 100 may finish the processing on the visible input image. The adjustment unit 130 may perform the above-described adjustment on the visible input image in a case where the first detection unit 140 detects the face from the visible input image.

The second detection unit 150 receives the near-infrared image from the second input unit 120. The second detection unit 150 detects a face from the received near-infrared image. A method by which the second detection unit 150 detects the face from the near-infrared image may be any of various existing methods.

In a case where the first detection unit 140 detects the face from the visible input image and further the second detection unit 150 detects the face from the near-infrared image, the alignment unit 160 performs alignment between the adjusted visible image and the near-infrared input image as follows, for example. For example, the alignment unit 160 specifies a relative position between the adjusted visible image and the near-infrared input image at which a difference (for example, an index indicating magnitude of the difference described later) in an overlaid portion in a case where the adjusted visible image is overlaid on the near-infrared input image is the smallest. The relative position may be represented by, for example, a vector representing translation. The relative position may also be represented by, for example, the translation and rotation (for example, an angle of the rotation). Various existing methods may be used as a method of specifying the relative position.

Specifically, for example, the alignment unit 160 may specify the relative position between the adjusted visible image and the near-infrared input image at which an average of absolute values of differences in pixel value of the respective overlaid pixels in the portion in which the adjusted visible image is overlaid on the near-infrared input image is the smallest. In this case, the index indicating the magnitude of the difference in the overlaid portion between the adjusted visible image and the near-infrared input image is the average of the absolute values of the differences in pixel value of the respective pixels. The index may be another index indicating the magnitude of the difference between the images.

The alignment unit 160 does not have to use the pixel having the pixel value included in the range of the bin including the peak of the dark portion and the pixel having the pixel value included in the range of the bin including the peak of the bright portion in the histogram of the adjusted visible image when calculating the difference between the adjusted visible image and the near-infrared input image. Similarly, the alignment unit 160 does not have to use the pixel having the pixel value included in the range of the bin including the peak of the dark portion and the pixel having the pixel value included in the range of the bin including the peak of the bright portion in the histogram of the near-infrared input image when calculating the difference between the adjusted visible image and the near-infrared input image. In a case where the pixel value of at least one of the pixel of the adjusted visible image and the pixel of the near-infrared input image overlaid on each other is included in any of the range including the peak of the bright portion and the range including the peak of the dark portion, the alignment unit 160 may exclude these pixels from the calculation of the difference between the pixel values. The alignment unit 160 may calculate the index indicating the magnitude of the difference between the images only from the pixels not excluded from the calculation of the difference between the pixel values, for example.

The first detection unit 140 may detect a feature point of the face from the visible input image and transmit information on the detected feature point of the face to the alignment unit 160. The information on the feature point is, for example, a position of the feature point in the image from which the feature point is extracted, a type of the feature point and the like. The information on the feature point is not limited to the above-described example. The second detection unit 150 may detect a feature point of the face from the near-infrared input image and transmit the detected feature point of the face to the alignment unit 160. The feature point of the face may be, for example, the feature point determined in advance such as an outer corner of an eye, an inner corner of the eye, a pupil, a corner of a mouth, and a head of a nose.

The alignment unit 160 may receive the information on the feature point of the face in the visible input image from the first detection unit 140 and receive the feature point of the face in the near-infrared input image from the second detection unit 150. Then, the alignment unit 160 calculates the relative position between the visible input image and the near-infrared input image in a case where the visible input image is overlaid on the near-infrared input image so that a difference in position between the related feature points of the face becomes the smallest. Specifically, the alignment unit 160 may calculate conversion of coordinates so that the coordinates of the feature point of the face detected in the visible input image become the coordinates of the feature point of the face related to the feature point of the face in the visible input image detected in the near-infrared input image. As a method of calculating the conversion of the coordinates, various existing methods may be applied.

The inversion unit 170 receives the adjusted visible image from the adjustment unit 130. The inversion unit 170 inverts the pixel value of the adjusted visible image, and generates an inverted visible image in which the pixel value of the adjusted visible image is inverted. The inversion of the pixel value may be, for example, subtracting the pixel value from the maximum value of the pixel value in the value range of the pixel values of the image. The inversion of the pixel value may be, for example, changing a positive sign of the pixel value to a negative sign.

The third detection unit 180 receives the inverted visible image from the inversion unit 170, and receives the input near-infrared image from the second input unit 120, for example. The third detection unit 180 further receives the relative position between the adjusted visible image and the near-infrared input image at which the difference of the overlaid portion in a case where the adjusted visible image is overlaid on the near-infrared input image is the smallest from the alignment unit 160. The third detection unit 180 generates a synthetic image obtained by overlaying the adjusted visible image on the near-infrared input image in a region in which the adjusted visible image and the near-infrared input image overlap with each other at the received relative position. Specifically, the third detection unit 180 calculates the sum of the adjusted visible image pixel value and the pixel value of the near-infrared input image at a position of each overlapping pixel in the region in which the adjusted visible image and the near-infrared input image overlap with each other, and generates the synthetic image in which the calculated sum is the pixel value of the pixel at the position. The overlapping pixels represent the pixels present at the same position in a case where the two images are overlaid on each other.

As described above, the human pupil has a retroreflection characteristic with respect to a near-infrared electromagnetic wave. Therefore, in the near-infrared input image, a region of the pupil becomes bright. However, since the human pupil does not have a retroreflection characteristic with respect to visible light, the region of the pupil becomes dark in the visible input image. In the inverted visible image, the region of the pupil is relatively bright. Therefore, in the synthetic image in which the pixel value of the inverted visible image and the pixel value of the near-infrared input image are added up for each related pixel, the region of the pupil is expected to be significantly bright.

The third detection unit 180 detects the pupil in the synthetic image. Specifically, first, the third detection unit 180 binarizes the synthetic image, for example. For example, the third detection unit 180 may set the pixel values of the pixels having the pixel values included in the bin of the peak of the brightness and the pixels having the pixel values brighter than those pixel values of the synthetic image to 1, for example, and set the pixel values of other pixels to 0, for example. The third detection unit 180 may determine a frequency threshold (for example, the multiplication by the constant less than one of the frequency of the peak, that is, the mode value) based on the frequency of the peak of the brightness. The third detection unit 180 may set the pixel values of the pixels of the synthetic image having the pixel values in a range of continuous bins in which the frequency exceeds the threshold, the range including the bin of the mode value, or the pixel values indicating that they are brighter than the pixel values represented by the bins to 1, and set the pixel values of other pixels to 0. The third detection unit 180 may binarize the synthetic image by another method. The third detection unit 180 may detect, as the region of the pupil, a connected region having a predetermined area or larger of the pixels in which the brighter pixel value of the two pixel values is set by binarization. The third detection unit 180 may detect, as the region of the pupil, a connected region an area of which is included in a predetermined range experimentally determined in advance, for example, out of the above-described connected region. The third detection unit 180 may detect, as the region of the pupil, a connected region in which a ratio of a minor radius to a major radius is smaller than a predetermined value out of the above-described connected region. In the following description, the third detection unit 180 may be expressed as a pupil detection unit 180.

The output unit 190 outputs information on the pupil detected by the third detection unit 180. Specifically, the output unit 190 may output information indicating the region of the pupil in the near-infrared input image. The information indicating the region of the pupil may be information capable of specifying the pixels included in the region detected as the region of the pupil (for example, a list of coordinates of the pixels included in the region detected as the region of the pupil). The information on the pupil may be, for example, information indicating a position of the pupil (for example, coordinates of the center of gravity and the like of the region representing the pupil). The information indicating the position of the pupil may be, for example, information indicating the position of the pupil in the near-infrared input image. The information indicating the position of the pupil may be, for example, information indicating the position of the pupil in the visible input image. The information indicating the pupil may include the relative position in addition to the information indicating the position of the pupil. The information indicating the position of the pupil may include the information indicating the position of the pupil in the near-infrared input image and the information indicating the position of the pupil in the visible input image. The information on the pupil may be other information.

Operation

Next, an operation of the image processing device 100 of the example embodiment is described in detail with reference to the drawings.

Figure 2:
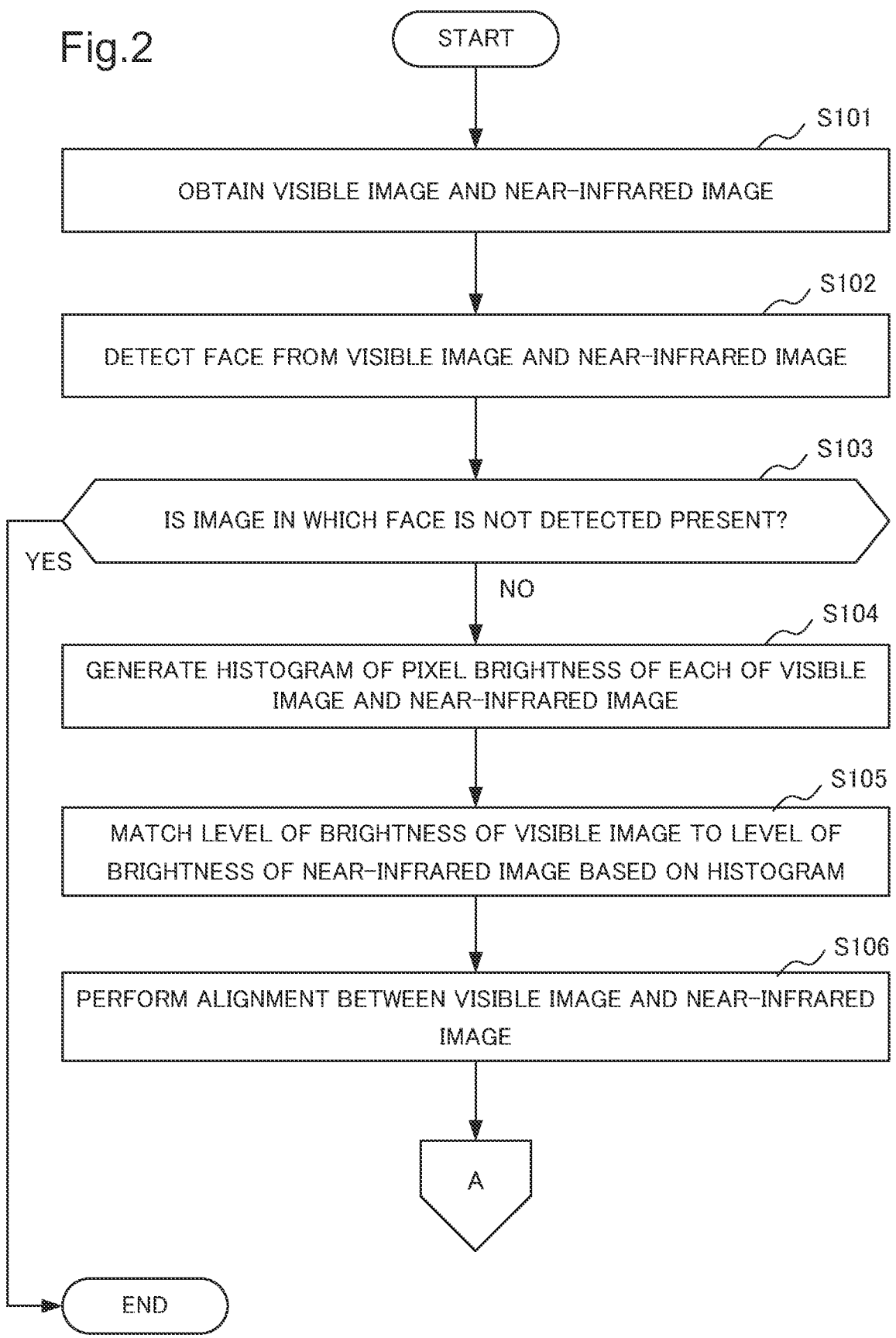
FIG. 2 is a flowchart illustrating an example of an operation of an image processing device of the first example embodiment of the disclosure.
Figure 3:
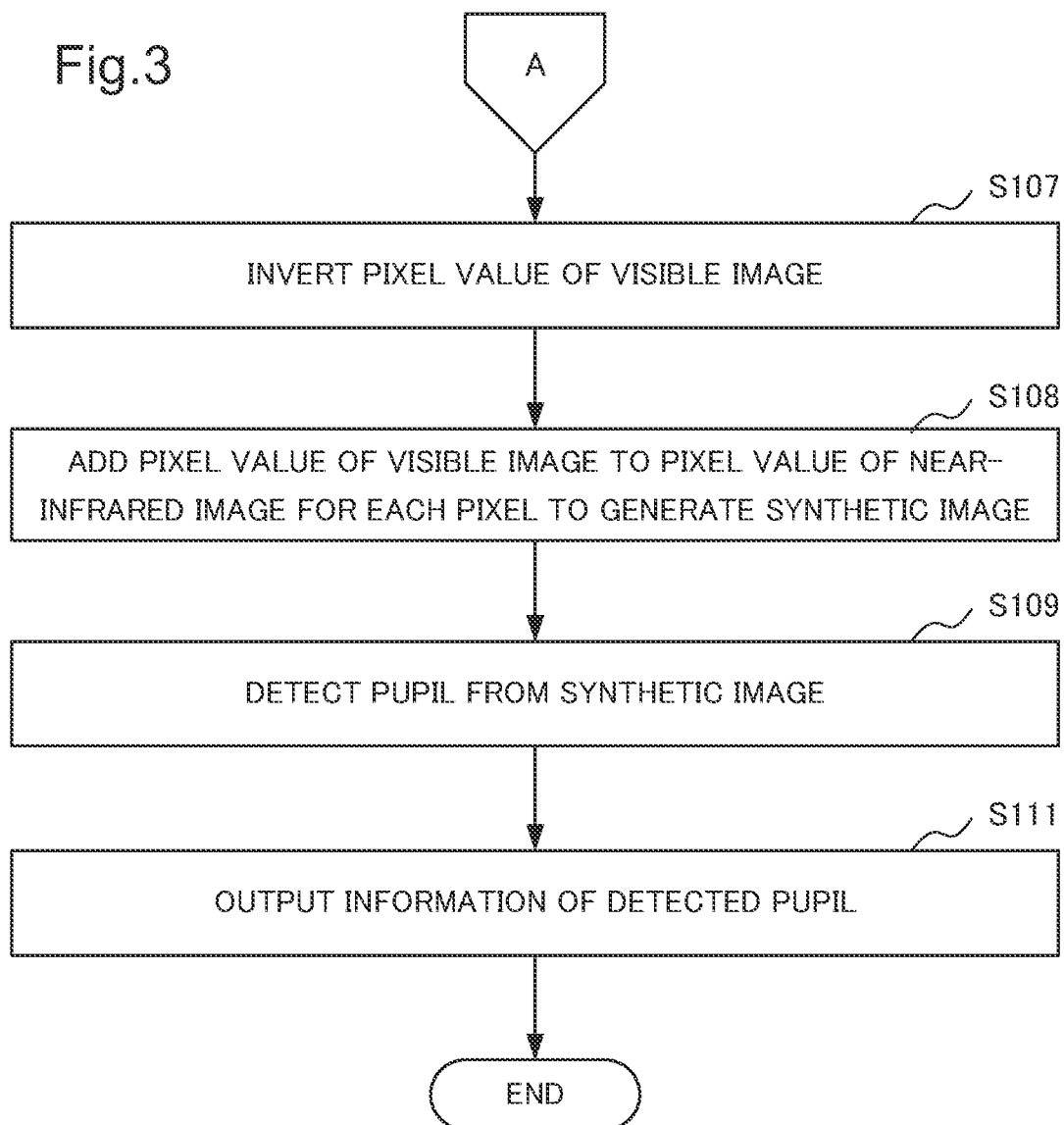
FIG. 3 is a flowchart illustrating an example of the operation of the image processing device of the first example embodiment of the disclosure.

FIGS. 2 and 3 are flowcharts illustrating an example of the operation of the image processing device 100 of the example embodiment.

In the operation illustrated in FIG. 2, first, the first input unit 110 obtains the visible image from the visible imaging device 200, for example, and the second input unit 120 obtains the near-infrared image from the near-infrared imaging device 300, for example (step S101). The visible image obtained at step S101 is the above-described visible input image. The near-infrared image obtained at step S101 is the above-described near-infrared input image.

Next, the first detection unit 140 detects the face in the visible image obtained by the first input unit 110. Then, the second detection unit 150 detects the face in the near-infrared image obtained by the second input unit 120 (step S102). In a case where there is the image in which no face is detected, that is, in a case where the face is not detected from either the visible image or the near-infrared image (YES at step S103), the image processing device 100 finishes the operation illustrated in FIGS. 2 and 3. In a case where the face is detected from both the visible image and the near-infrared image, the image processing device 100 then performs the operation at step S104.

The adjustment unit 130 generates the histogram of brightness of the pixels of each of the visible image and the near-infrared image (step S104). The adjustment unit 130 matches the level of brightness of the visible image to the level of brightness of the near-infrared image based on the generated histogram (step S105). At step S105, the adjustment unit 130 adjusts the pixel values of the visible image (herein, the visible input image) so that the histogram of the range excluding the range including the peak of the dark portion and the range including the peak of the bright portion approaches the histogram of the near-infrared input image, for example, as described above. Then, the adjustment unit 130 generates the adjusted visible image in which the pixel values are adjusted in such a manner.

Next, the alignment unit 160 performs alignment between the visible image and the near-infrared image (step S106). The visible image at step S106 is the adjusted visible image generated by the adjustment unit 130. The near-infrared image at step S106 is the near-infrared input image. In the alignment at step S106, the alignment unit 160 derives the relative position between the adjusted visible image and the near-infrared input image in which the difference in the overlapped portion between the adjusted visible image and the near-infrared input image is the smallest. After the operation at step S106, the image processing device 100 performs the operation at step S107 illustrated in FIG. 3.

In the operation illustrated in FIG. 3, next, the inversion unit 170 inverts the pixel value of the visible image (step S107). The visible image at step S107 is the adjusted visible image generated by matching the level of brightness at step S105.

Next, the third detection unit 180 adds up the pixel values of the overlaid pixels for each pixel in the overlaid portion between the adjusted visible image and the near-infrared input image at the relative position obtained by the alignment at step S106, thereby generating the synthetic image (step S108). The third detection unit 180 detects the pupil from the synthetic image (step S109).

Then, the output unit 190 outputs the information on the detected pupil (step S110).

Effect

The example embodiment described above has an effect of reducing a cost for detecting the pupil. This is because the adjustment unit 130 performs the adjustment to match the level of brightness of the visible image to the level of brightness of the near-infrared image, and the alignment unit 160 performs the alignment of the visible image and the near-infrared image. Therefore, it is not necessary to adjust so that optical axes of four devices including the two light sources and the two imaging devices to be the same. Therefore, a device such as a half mirror that bends the optical axis is not necessary. It is not necessary to correctly arrange the two light sources, the two imaging devices, a plurality of half mirrors and the like. Therefore, the cost for detecting the pupil may be reduced.

The example embodiment also has an effect of improving performance of the pupil detection. This is because the adjustment unit 130 adjusts the pixel values based on the histogram of the range other than the range including the peak of the dark portion and the range including the peak of the bright portion. This is because the alignment unit 160 also performs the alignment using the pixels other than the pixels having the pixel values included in the range of the pixel values including the peak of the dark portion and the range of the pixel values including the peak of the bright portion of the histogram.

Since the pupil has the retroreflection characteristic with respect to the near-infrared light, the region of the pupil in the near-infrared input image is bright. In other words, the pixel value of the pixel included in the region of the pupil of the near-infrared input image takes a value indicating that this is bright. The pupil does not have the retroreflection characteristic with respect to the visible light. Therefore, in the visible input image, the region of the pupil is dark. In other words, the pixel value of the pixel included in the region of the pupil takes a value indicating that this is dark. In the region other than the pupil, it may be considered that the region dark in the visible input image and the adjusted visible image and bright in the near-infrared input image is not normally present. In the adjusted visible image adjusted by the adjustment unit 130 and the near-infrared input image, the distribution of the pixel values is close in the pixels having the pixel values excluding the pixel value appearing as the peak of the dark portion and the pixel value appearing as the peak of the bright portion of the histogram.

In the visible image (visible input image and adjusted visible image), the peak of the bright portion is related to, for example, the pixel value of a shadow region, and the peak of the dark portion is related to, for example, the pixel value of a region of reflection by glasses or reflection by tears. In the near-infrared input image, the peak of the bright portion is related to, for example, the pixel value of the region of the pupil or the reflection by the glasses, and the peak of the dark portion is related to, for example, the pixel value of a portion at low temperature. An angle of the reflection by the glasses varies depending on the wavelength. Therefore, the region of the reflection by the glasses in the visible image is different from the region of the reflection by the glasses in the near-infrared image.

In the example embodiment, since it is possible to suppress an effect on the adjustment of the pixel value and alignment in the region in which the brightness is significantly different between the visible image and the near-infrared image such as the region of the reflection by the glasses, it is possible to improve accuracy of the adjustment of the pixel value and accuracy of the alignment. Therefore, in the example embodiment, the accuracy of the pupil detection may be improved.

First Variation of First Example Embodiment

Next, a first variation of the first example embodiment of the disclosure is described in detail with reference to the drawings. First, a configuration of this variation is described, and next, an operation of this variation is described.

Configuration

Figure 4:
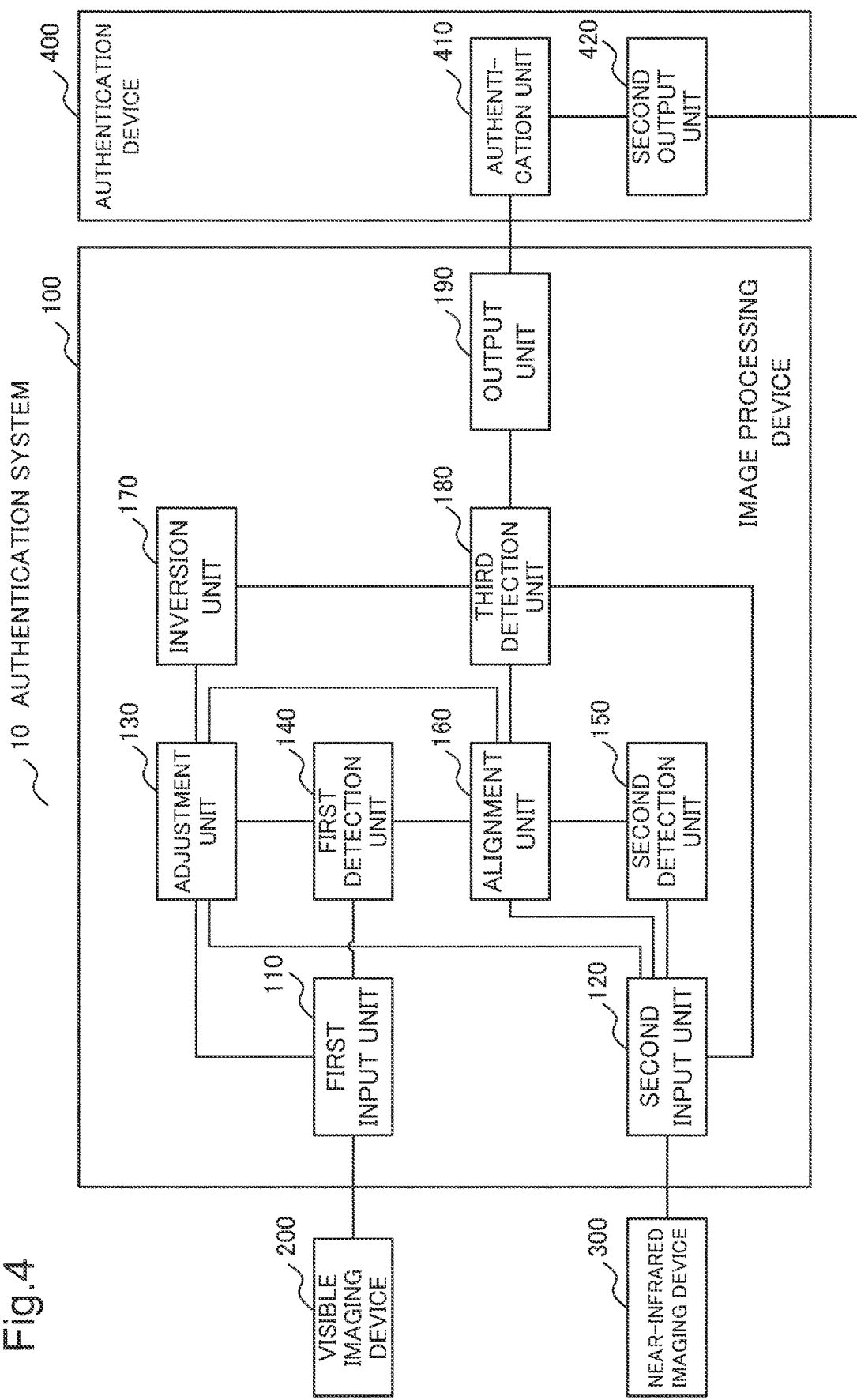
FIG. 4 is a block diagram illustrating an example of a configuration of an authentication system of first and second variations of the first example embodiment of the disclosure.

FIG. 4 is a block diagram illustrating an example of a configuration of an authentication system 10 of this variation.

The authentication system 10 illustrated in FIG. 4 includes an image processing device 100, which is a pupil detection device, a visible imaging device 200, a near-infrared imaging device 300, and an authentication device 400. The image processing device 100, the visible imaging device 200, and the near-infrared imaging device 300 are the same as the image processing device 100, the visible imaging device 200, and the near-infrared imaging device 300 of the first example embodiment, respectively. The authentication device 400 is communicably connected to the image processing device 100. The authentication device 400 may be included in the image processing device 100. In other words, the image processing device 100 may further operate as the authentication device 400.

An output unit 190 of this variation outputs information on a detected pupil and a face image. The output unit 190 of this variation may output information on a position of the pupil as the information on the pupil. The face image may be a visible input image obtained and output by the visible imaging device 200. In that case, the visible input image may be transmitted to the output unit 190 via, for example, a first input unit 110, a first detection unit 140, an alignment unit 160, and a third detection unit 180. The visible input image may be transmitted from the first input unit 110 to the output unit 190 via a path not illustrated in FIG. 4 for simplicity. The face image may be an adjusted visible image adjusted by an adjustment unit 130. In that case, the adjusted visible image may be transmitted to the output unit 190 via the alignment unit 160 and the third detection unit 180, for example. The adjusted visible image may be transmitted from the adjustment unit 130 to the output unit 190 via a path not illustrated in FIG. 4 for simplicity. The face image may be a near-infrared input image obtained and output by the near-infrared imaging device 300. In that case, the near-infrared input image may be transmitted from a second input unit 120 to the output unit 190 via the alignment unit 160 and the third detection unit 180. The infrared input image may be transmitted from the second input unit 120 to the output unit 190 via the third detection unit 180. The near-infrared input image may be transmitted from the second input unit 120 to the output unit 190 via a path not illustrated in FIG. 4 for simplicity. A type of the image transmitted as the face image may be determined in advance.

The authentication device 400 includes an authentication unit 410 and a second output unit 420.

The authentication unit 410 receives the information on the detected pupil (for example, the information on the position of the detected pupil) and the face image from the output unit 190 of the image processing device 100. The authentication unit 410 specifies a position of an authentication site in the face image based on the received information on the pupil, for example. The authentication unit 410 performs authentication based on an image of the authentication site the position of which is specified. The authentication site is at least a part of the face used for the authentication. The authentication site may be, for example, an iris. The authentication site may be, for example, the face. The authentication site may be determined in advance. The authentication unit 410 performs the authentication by any of existing authentication methods using the image of the authentication site. Specifically, the authentication unit 410 extracts an image of a region of the authentication site according to the authentication method from the face image, and extracts a feature amount according to the authentication method from the extracted region, for example. Then, the authentication unit 410 performs the authentication using the extracted feature amount. It is hereinafter described more specifically.

In a case where the authentication site is the iris, the authentication unit 410 may extract a region of the iris from the periphery of the region of the pupil. In a case where the authentication site is the face, a region in which a region of the face may be present may be estimated based on the position of the detected pupil, and the region of the face may be extracted from the estimated region. In a case where the authentication site is the face, another feature point of the face may be extracted based on the position of the detected pupil. As the authentication method by the authentication unit 410, various existing methods according to the authentication site may be applied.

The authentication unit 410 extracts the feature amount according to the authentication method from the image of the region of the authentication site. The authentication unit 410 compares the extracted feature amount with, for example, the feature amount registered in advance in the authentication unit 410. The authentication unit 410 determines whether a person of the face image from which the extracted feature amount is extracted is the same as the person of the face image from which the feature amount registered in advance is extracted based on a result of the comparison.

The second output unit 420 outputs a result of the authentication by the authentication unit 410.

Operation

Figure 5:
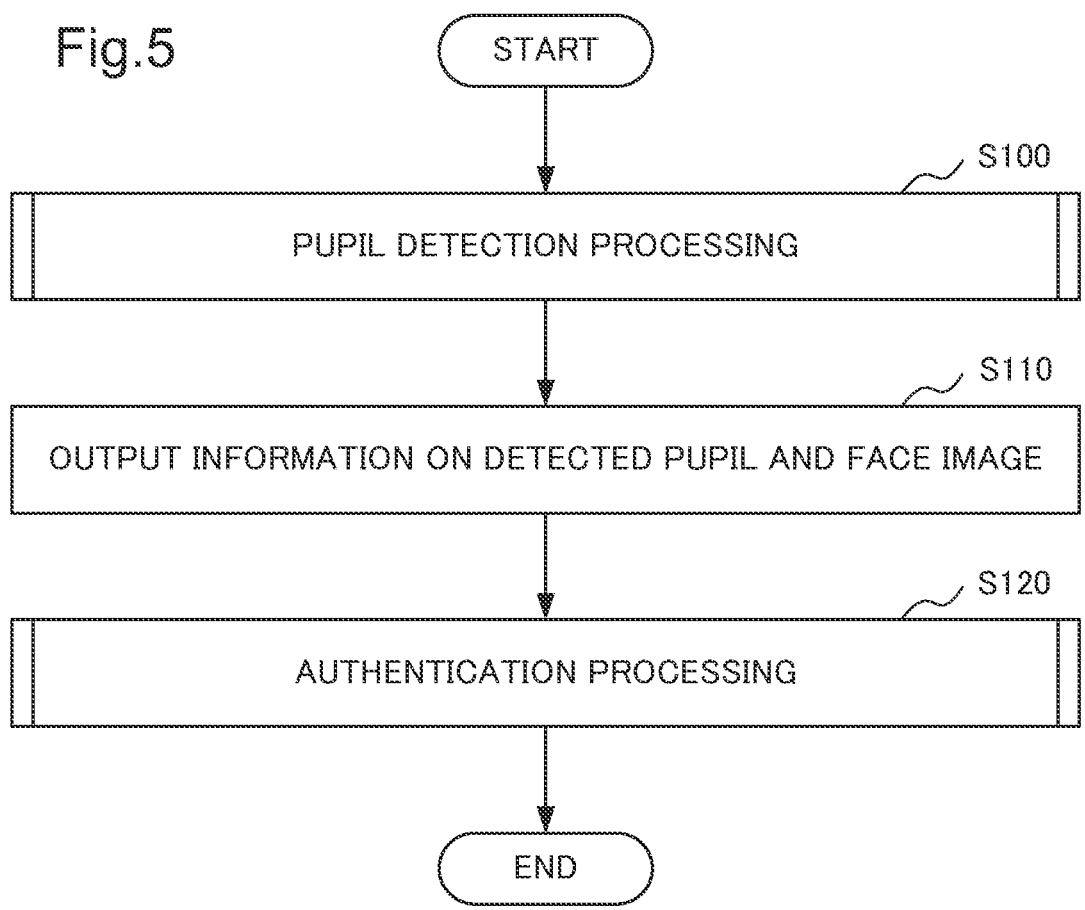
FIG. 5 is a flowchart illustrating an entire example of an operation of the authentication system of the first and second variations of the first example embodiment of the disclosure.

FIG. 5 is a flowchart illustrating an entire example of an operation of the authentication system 10 of this variation.

In the operation illustrated in FIG. 5, first, the image processing device 100 performs pupil detection processing (step S100). The pupil detection processing is described later. The above-described information on the pupil is obtained by the pupil detection processing. The output unit 190 outputs the information on the detected pupil (for example, the information on the position of the detected pupil) and the face image to the authentication device 400 (step S110). Then, the authentication device 400 performs authentication processing (step S120). The authentication processing is described later.

Figure 6:
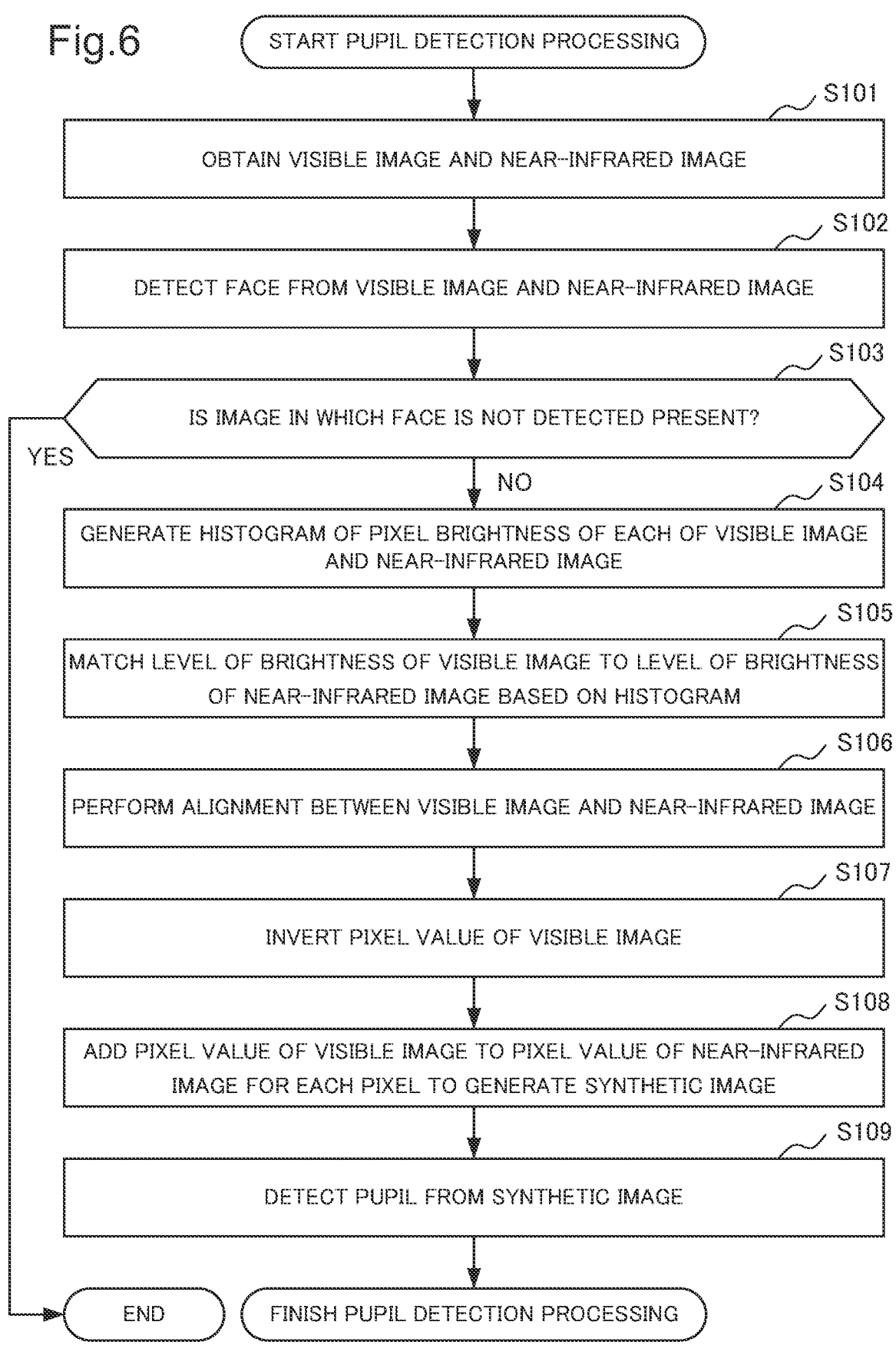
FIG. 6 is a flowchart illustrating an example of an operation of pupil detection processing of an image processing device 100 of first to fourth variations of the first example embodiment of the disclosure.

FIG. 6 is a flowchart illustrating an example of an operation of the pupil detection processing of the image processing device 100 of this variation. The operation from step S101 to step S109 illustrated in FIG. 6 is the same as the operation from step S101 to step S109 of the image processing device 100 of the first example embodiment illustrated in FIGS. 2 and 3. After the operation at step S109, the image processing device 100 finishes the pupil detection processing illustrated in FIG. 6.

Figure 7:
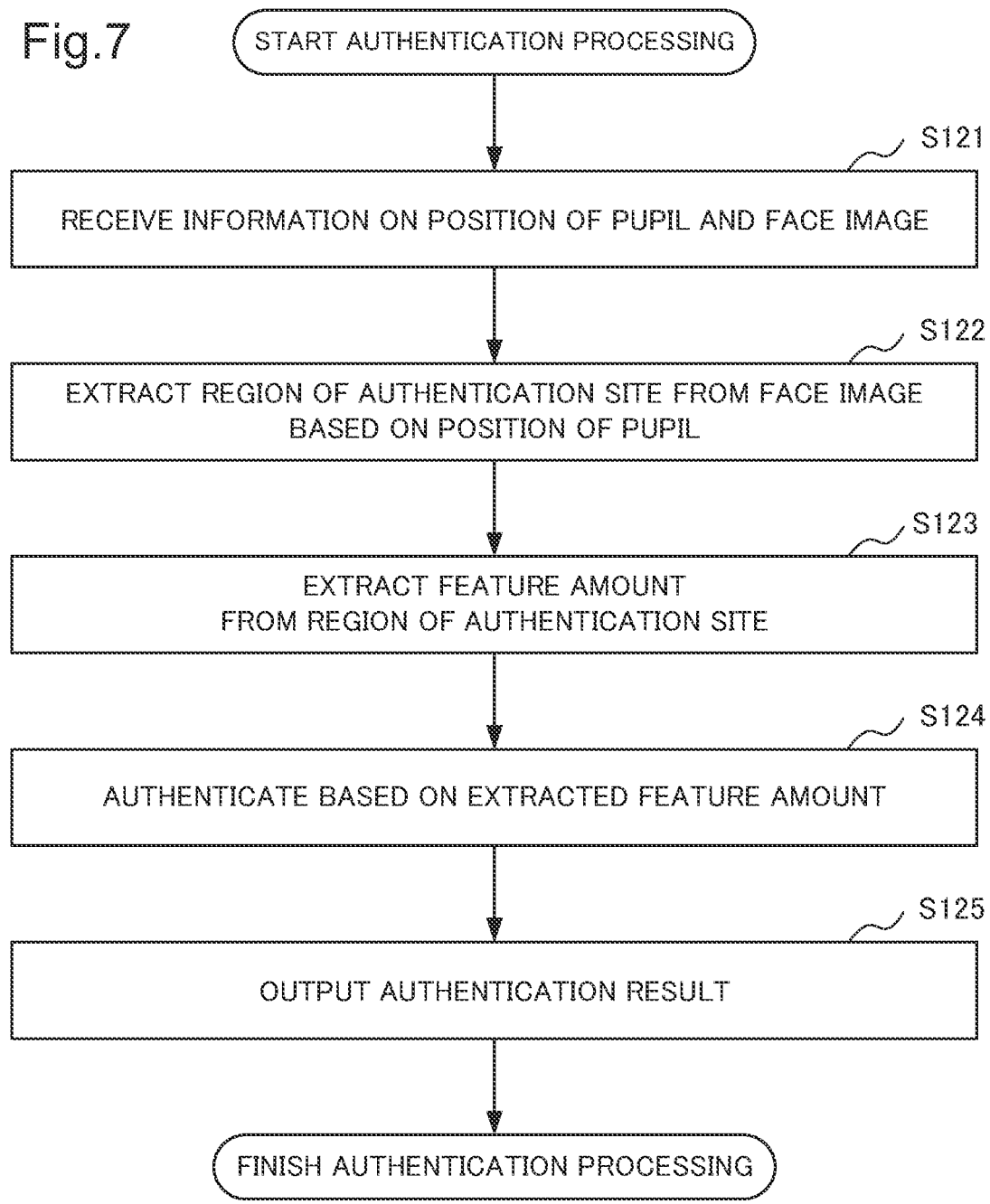
FIG. 7 is a flowchart illustrating an example of an operation of authentication processing of an authentication device of the first and fourth variations of the first example embodiment of the disclosure.

FIG. 7 is a flowchart illustrating an example of the operation of the authentication processing of the authentication device 400 of this variation. In the operation illustrated in FIG. 7, first, the authentication unit 410 receives the information on the position of the pupil and the face image (step S121). Next, the authentication unit 410 extracts the region of the authentication site from the face image based on the position of the pupil (step S122). The authentication unit 410 extracts the feature amount from the extracted region of the authentication site (step S123). The authentication unit 410 performs the authentication based on the extracted feature amount (step S124). The second output unit 420 outputs the result of the authentication (step S125).

Second Variation of First Example Embodiment

Next, a second variation of the first example embodiment is described.

Configuration

FIG. 4 is a block diagram illustrating a configuration of an authentication system 10 of this variation. The configuration of the authentication system 10 of this variation is the same as the configuration of the authentication system 10 of the first variation of the first example embodiment. This variation is the same as the first variation of the first example embodiment except for a difference described below.

An output unit 190 of an image processing device 100 outputs a near-infrared input image as a face image.

An authentication unit 410 of an authentication device 400 extracts an iris as an authentication site. The authentication unit 410 changes a pixel value of a region of a pupil of the near-infrared input image to another value. The another value may be, for example, the pixel value indicating brightness darker than brightness indicated by an average of the pixel values of the pixels in a region of the iris. The another value may be the pixel value indicating brightness darker than brightness indicated by the pixel value of the region of the pupil of the near-infrared input image. The another value may be experimentally determined in advance. By changing the pixel value of the region of the pupil so that the brightness indicated by the pixel value becomes dark, it is possible to reduce an adverse effect such as a decrease in authentication system because the region of the pupil is bright. The authentication unit 410 performs iris authentication as the authentication.

Operation

FIG. 5 is a flowchart illustrating an operation of the authentication system 10 of this variation. An entire operation of the authentication system 10 of this variation is the same as the entire operation of the authentication system 10 of the first variation of the first example embodiment. The operation at steps S100 and S110 of the authentication system 10 of this variation is the same as the operation at steps S100 and S110 of the authentication system 10 of the first variation of the first example embodiment. However, the face image output at step S110 is the near-infrared input image. The operation of authentication processing at step S120 of the authentication system 10 of this variation is different from the operation of the authentication processing at step S120 of the authentication system 10 of the first variation of the first example embodiment.

Figure 8:
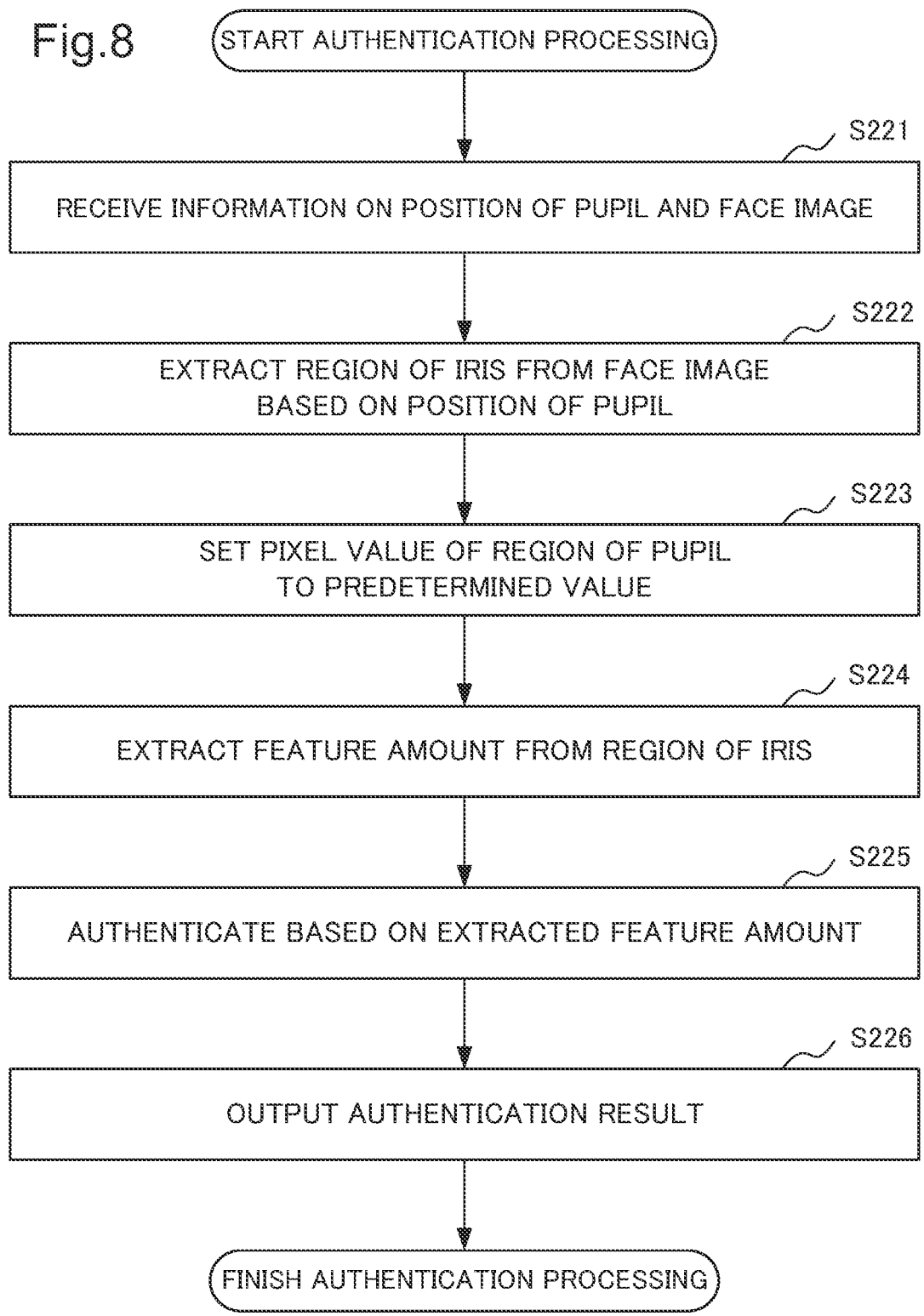
FIG. 8 is a flowchart illustrating an example of an operation of authentication processing of an authentication device of the second variation of the first example embodiment of the disclosure.

FIG. 8 is a flowchart illustrating an example of the operation of the authentication processing of the authentication system 10 of this variation. In the operation illustrated in FIG. 8, the authentication unit 410 receives information on a position of the pupil and the face image (step S221). The face image received at step S221 is the near-infrared input image. Next, the authentication unit 410 extracts the region of the iris from the face image based on the information on the position of the pupil (step S222). The authentication unit 410 sets the pixel value of the region of the pupil to another value (for example, a predetermined value) (step S223). The authentication unit 410 extracts a feature amount from the region of the iris (step S224). The authentication unit 410 performs the authentication based on the extracted feature amount (step S225). The second output unit 420 outputs a result of the authentication (step S226).

Third Variation of First Example Embodiment

Next, a third variation of the first example embodiment is described.

Configuration

Figure 9:
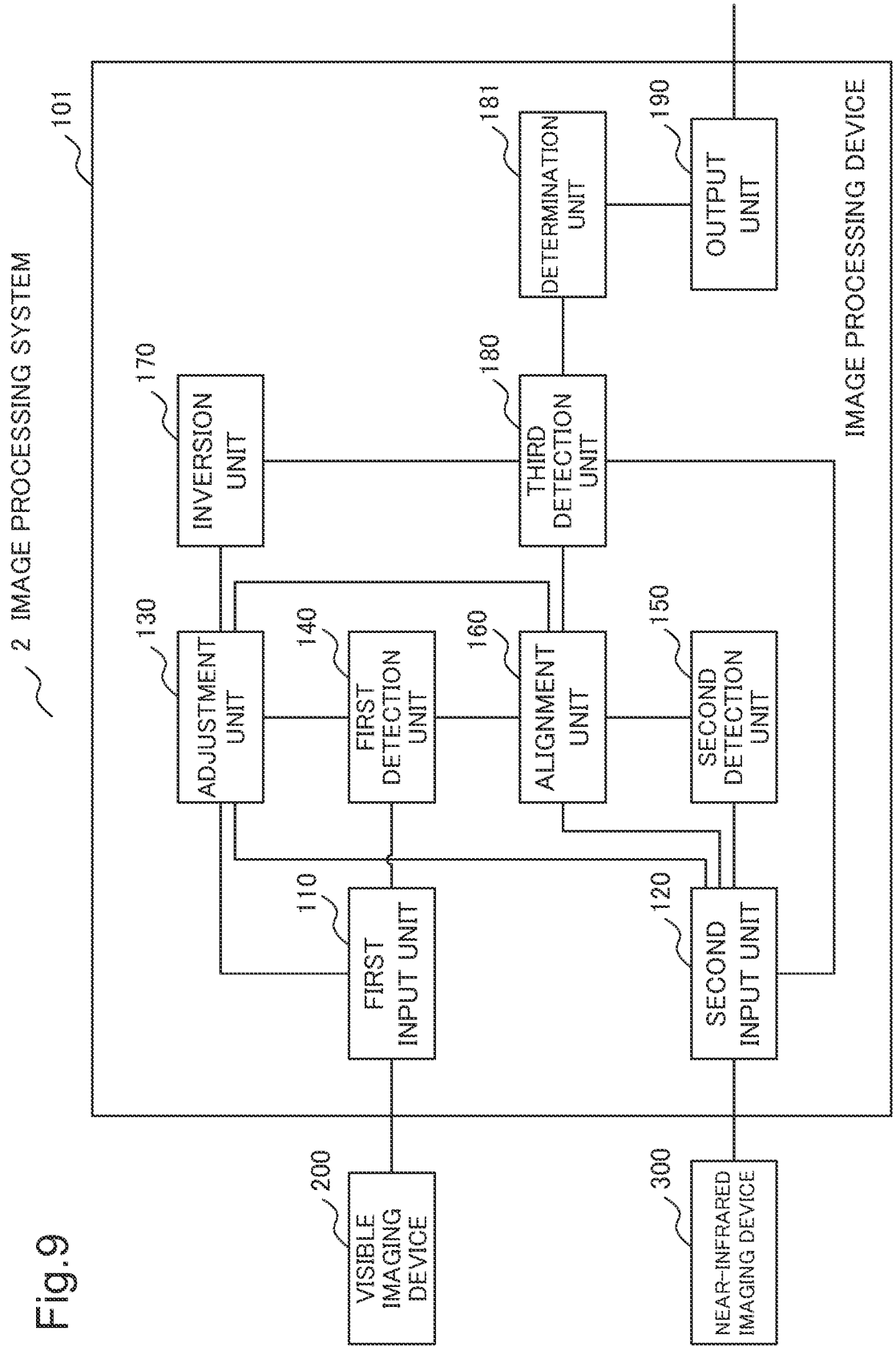
FIG. 9 is a block diagram illustrating an example of a configuration of an image processing system of the third variation of the first example embodiment of the disclosure.

FIG. 9 is a block diagram illustrating an example of a configuration of an image processing system 2 of this variation. The image processing system 2 includes an image processing device 101, a visible imaging device 200, and a near-infrared imaging device 300. The image processing device 101 is connected to the visible imaging device 200 so that a visible image obtained by the visible imaging device 200 may be obtained. The image processing device 101 is connected to the near-infrared imaging device 300 so that a near-infrared image obtained by the near-infrared imaging device 300 may be obtained. The image processing device 101 of this variation includes the same components as the components of the image processing device 100 of the first example embodiment, and a determination unit 181.

A third detection unit 180 transmits a visible image and information on a detected pupil to the determination unit 181. The third detection unit 180 may transmit an inverted visible image as the visible image to determination unit 181. The third detection unit 180 may transmit an adjusted visible image as the visible image to determination unit 181. The third detection unit 180 may transmit a visible input image as the visible image to the determination unit 181. A type of the visible image transmitted by the third detection unit 180 may be determined in advance. The information on the pupil includes information specifying a position of the pupil in the visible image. The information on the pupil may include, for example, information indicating the position of the pupil in the visible image. The information on the pupil may include, for example, a relative position and information indicating the position of the pupil in the near-infrared input image. The relative position is the above-described relative position. Specifically, the relative position is the relative position between the adjusted visible image and the near-infrared input image at which a difference in an overlaid portion between the adjusted visible image and the near-infrared input image is the smallest.

The determination unit 181 receives the visible image and the information on the detected pupil. The determination unit 181 detects the pupil at the position of the pupil specified by the information on the pupil in the visible image. In other words, it is determined whether there is the pupil at the position of the detected pupil in the visible image.

For example, in a case where a person to be imaged whose face image is captured wears sunglasses, in the visible image, a region of an eye is shielded by the sunglasses that absorb visible light, so that a difference in brightness between the iris and the pupil becomes small. In a case where the sunglasses are dark colored sunglasses, there is a case where there is no clear difference in brightness between the iris and the pupil. In a case where the sunglasses are darker colored sunglasses, there is a case where the difference in brightness of a portion shielded by the sunglasses cannot be confirmed. In general, however, the sunglasses often transmit near-infrared light. In other words, transmittance of the sunglasses to an electromagnetic wave having a near-infrared wavelength is often higher than transmittance to visible light. In such a case, if there is a bright region due to retroreflection of the pupil in the near-infrared input image, the pupil may be detected from a synthetic image.

For example, the determination unit 181 may detect the pupil based on a difference between brightness of the region of the detected pupil and, for example, brightness of a region around the region of the pupil (that is, a region corresponding to a region of the iris) in the visible image. Specifically, for example, in a case where a difference between an average of the pixel values of the pixels in the region of the pupil and an average of the pixel values of the pixels in the region around the region of the pupil in the visible image is smaller than a predetermined threshold, the determination unit 181 may determine that the pupil is not detected. That is, in this case, the determination unit 181 may determine that the sunglasses are present. In other words, in this case, the determination unit 181 may detect the sunglasses. For example, in a case where the difference between the average of the pixel values of the pixels in the region of the pupil and the average of the pixel values of the pixels in the region around the region of the pupil in the visible image is equal to more than the above-described threshold, the determination unit 181 may determine that the pupil is detected. That is, in this case, the determination unit 181 may determine that the sunglasses are not present. In other words, in this case, the determination unit 181 may determine that the sunglasses are not detected.

An output unit 190 outputs a result of the detection of the sunglasses. In a case where the authentication device 400 of the first or second variation described above is connected to the image processing device 101, the output unit 190 may output information necessary for the authentication device 400 to perform authentication.

Operation

Next, an operation of the image processing device 101 of this variation is described.

Figure 10:
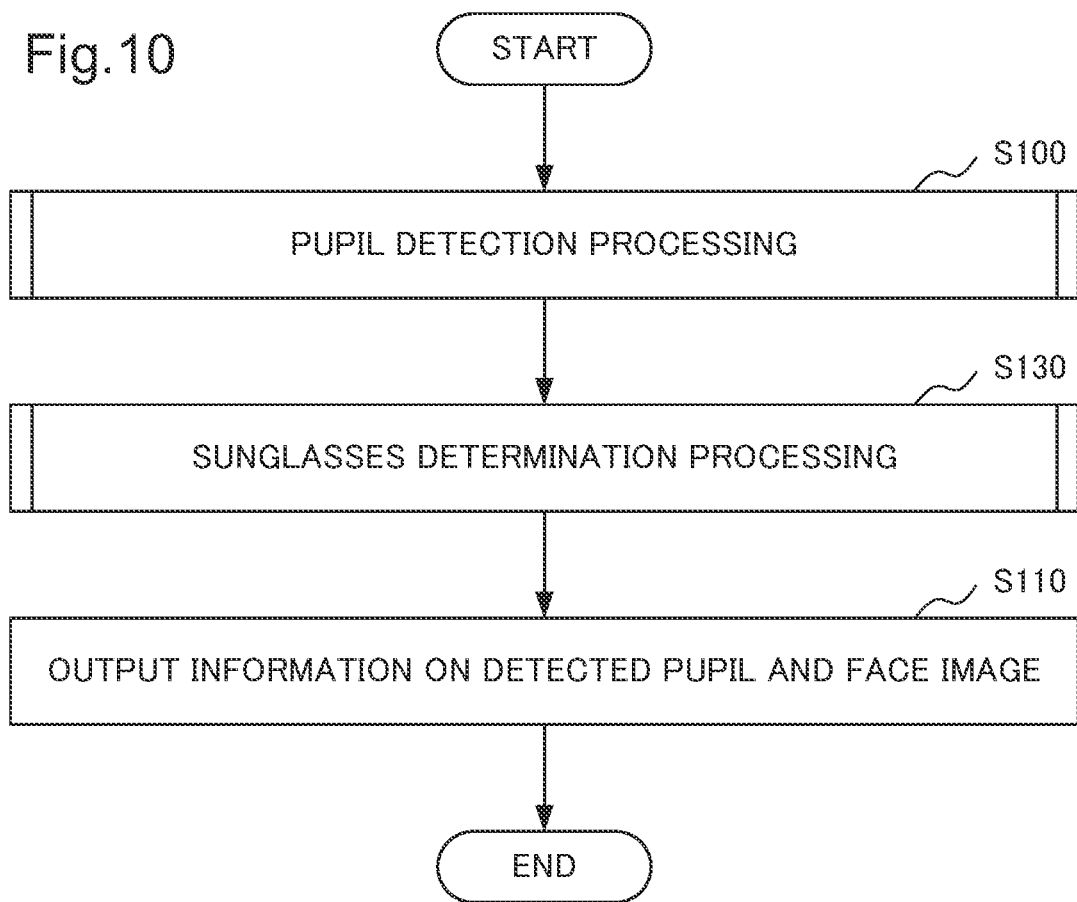
FIG. 10 is a flowchart illustrating an entire example of an operation of the image processing system of the third variation of the first example embodiment of the disclosure.

FIG. 10 is a flowchart illustrating an example of an entire operation of the image processing device 101 of this variation. In the operation illustrated in FIG. 10, the image processing device 101 performs pupil detection processing (step S100). The pupil detection processing at step S100 is the same as the pupil detection processing of the image processing device 100 of the first variation and the second variation of the first example embodiment at step S100 illustrated in FIG. 5. Next, the image processing device 101 performs sunglasses determination processing (step S130). The sunglasses determination processing is described later in detail. The image processing device 101 may further output the information on the detected pupil and the face image (step S110). The operation at step S110 of the image processing device 101 of this variation is the same as the operation at step S110 illustrated in FIG. 5 of the image processing device 100 of the first variation and the second variation of the first example embodiment.

Figure 11:
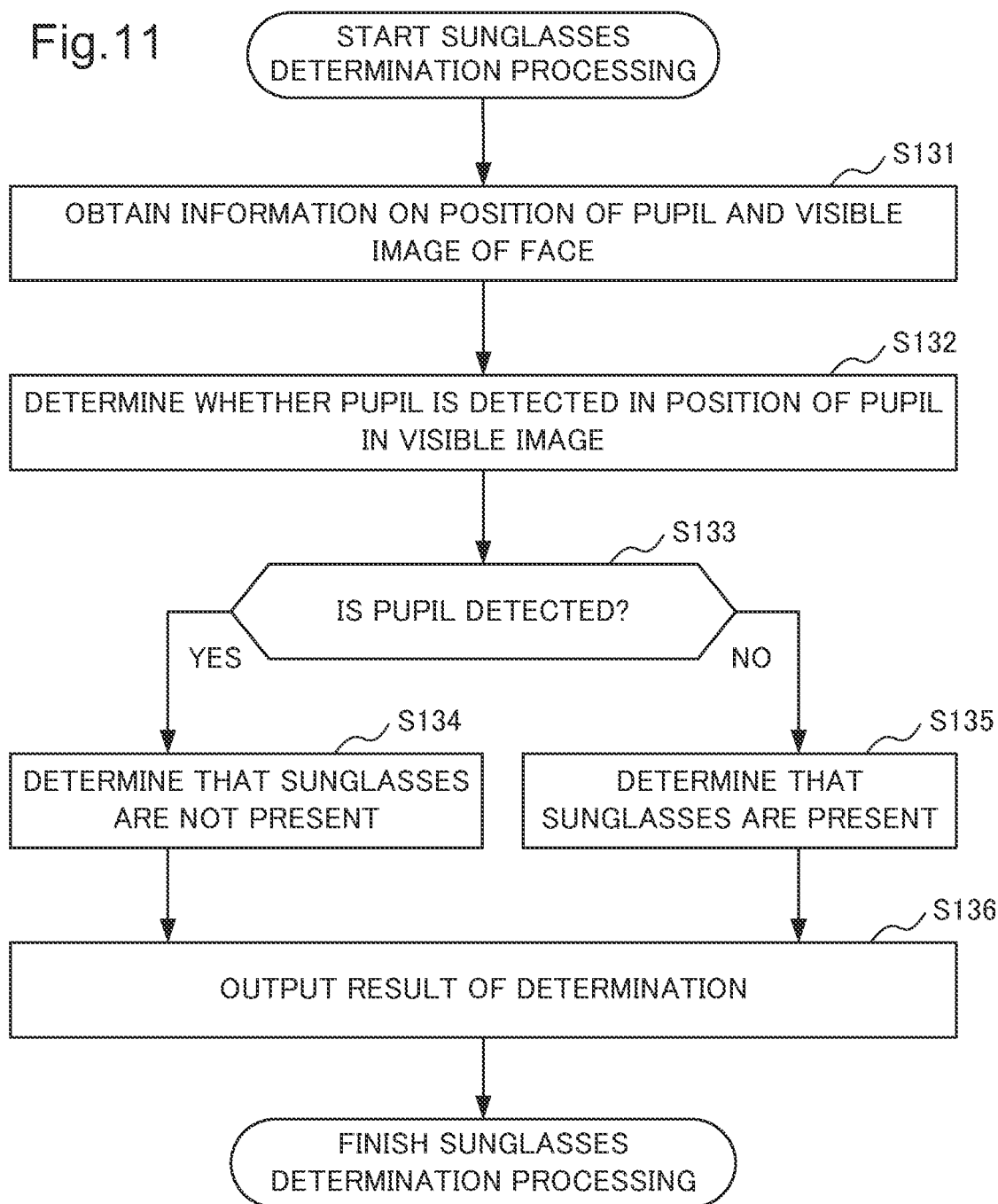
FIG. 11 is a flowchart illustrating an entire example of an operation of sunglasses determination processing of the image processing system of the third variation of the first example embodiment of the disclosure.

FIG. 11 is a flowchart illustrating an example of an operation of the sunglasses determination processing of the image processing device 100 of this variation. In the operation illustrated in FIG. 11, the determination unit 181 first obtains the information on the position of the pupil and the visible image of the face (step S131). The visible image of the face is the above-described visible input image, adjusted visible image, or inverted visible image. The information on the position of the pupil is the information capable of specifying the position of the detected pupil in the visible image. The determination unit 181 determines whether the pupil is detected at the position of the pupil in the visible image (step S132). In a case where the pupil is detected (YES at step S133), the determination unit 181 determines that the sunglasses are not present (step S134). In a case where the pupil is not detected (NO at step S133), the determination unit 181 determines that the sunglasses are present (step S135). The output unit 190 outputs a result of determination as to whether the sunglasses are present (step S136).

Fourth Variation of First Example Embodiment

Next, a fourth variation of the first example embodiment is described.

Configuration

Figure 12:
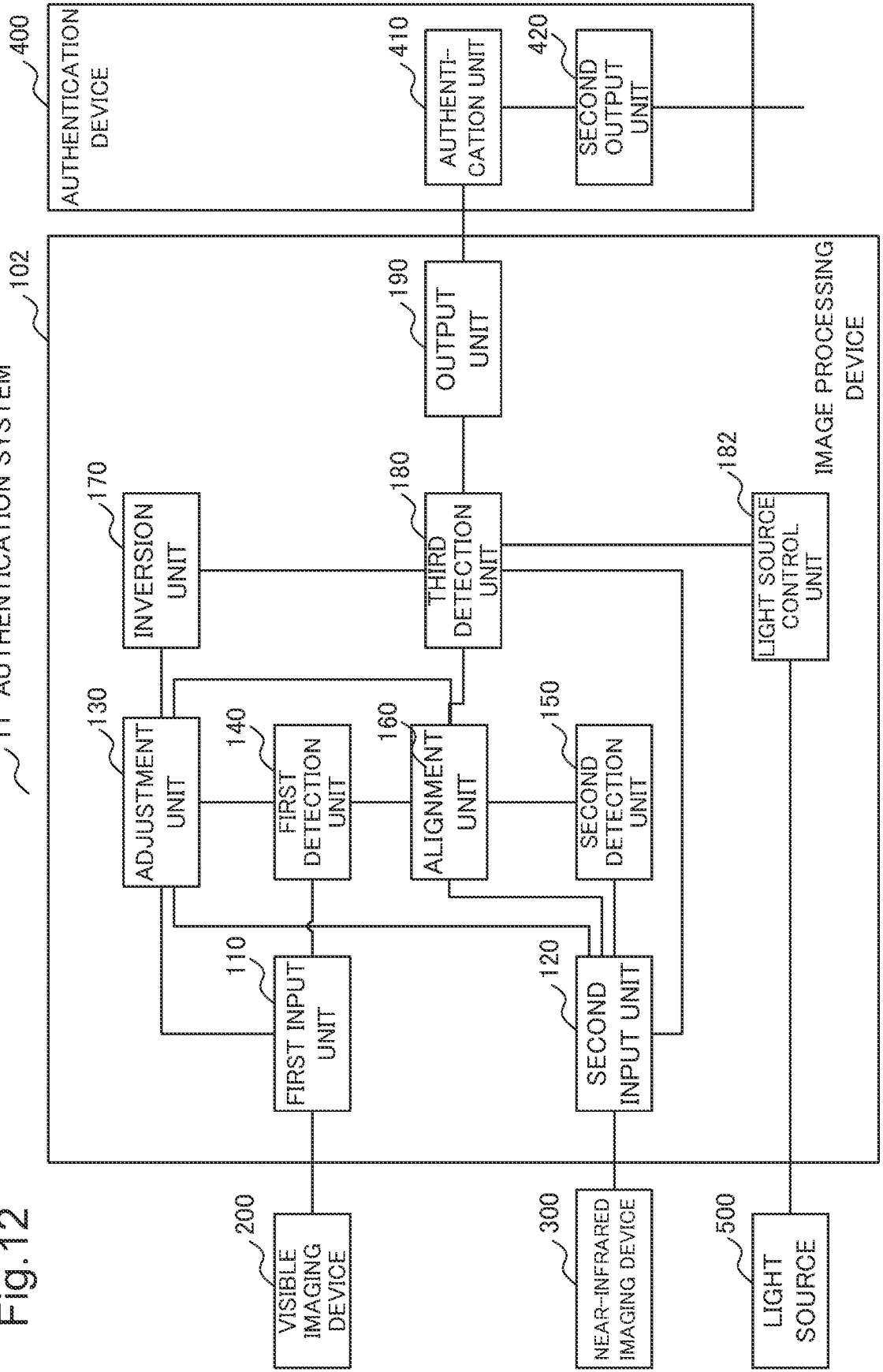
FIG. 12 is a block diagram illustrating an example of a configuration of an authentication system of the fourth variation of the first example embodiment of the disclosure.

FIG. 12 is a block diagram illustrating a configuration of an authentication system 11 of this variation. The authentication system 11 illustrated in FIG. 12 includes an image processing device 102, a visible imaging device 200, a near-infrared imaging device 300, an authentication device 400, and a light source 500. The visible imaging device 200 and the near-infrared imaging device 300 of this variation are the same as the visible imaging device 200 and the near-infrared imaging device of the first example embodiment. The authentication device 400 of this variation is the same as the authentication device 400 of the first variation of the first example embodiment. The authentication device 400 of this variation may be the same as the authentication device 400 of the second variation of the first example embodiment. The light source 500 is a light source that emits near-infrared light. The light source 500 is configured to be able to externally control intensity of the emitted near-infrared light.

The image processing device 102 includes the same components as the components of the image processing device 100 of the first example embodiment, and a light source control unit 182.

A third detection unit 180 of this variation operates similarly to the third detection unit 180 of the first example embodiment. The third detection unit 180 of this variation further determines whether a pupil is detected at a position of a detected pupil in a visible image. The visible image may be any one of a visible input image, an adjusted visible image, and an inverted visible image. The visible image in which it is determined whether the pupil is detected by the third detection unit 180 may be determined in advance. A method of determining whether the pupil is detected from the visible image by the third detection unit 180 of this variation may be the same as the method of determining whether the pupil is detected from the visible image by the determination unit 181 of the third variation. In a case where it is determined that the pupil is not detected from the visible image, the third detection unit 180 transmits, to the light source control unit 182, an instruction to control to increase intensity of the near-infrared light emitted by the light source 500.

The light source control unit 182 controls the light source 500, for example, in accordance with the instruction from the third detection unit 180. Specifically, the light source control unit 182 controls the intensity of the light (that is, the near-infrared light) emitted by the light source 500. The light source control unit 182 may be configured to increase the intensity of the light emitted by the light source 500 by a predetermined amount, for example, when receiving the instruction from the third detection unit 180. After the light source control unit 182 increases the intensity of the light emitted by the light source 500, the image processing device 102 obtains the visible input image and a near-infrared input image again, and detects the pupil based on the obtained visible input image and near-infrared input image. At that time, the light source control unit 182 may instruct a first input unit 110 to obtain the visible input image and instruct a second input unit 120 to obtain the near-infrared input image via a path not illustrated in FIG. 12 for simplicity. The first input unit 110 and the second input unit 120 may be configured to periodically obtain the respective images.

Operation

Next, an operation of the authentication system 11 of this variation is described.

Figure 13:
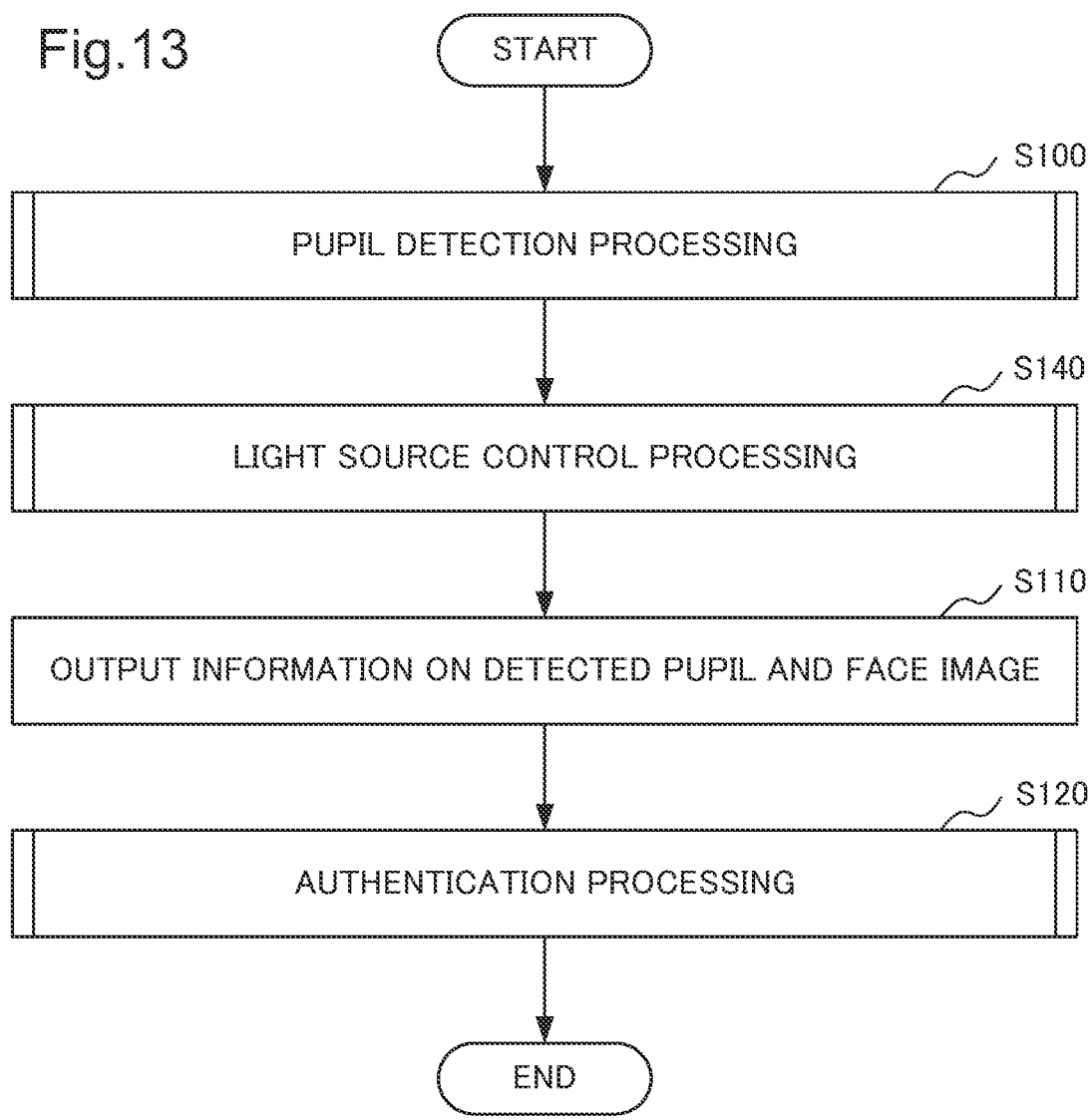
FIG. 13 is a flowchart illustrating an entire example of an operation of an authentication system of the fourth variation of the first example embodiment of the disclosure.

FIG. 13 is a flowchart illustrating an example of the operation of the authentication system 11 of this variation. In the example of the operation illustrated in FIG. 13, the image processing device 102 performs pupil detection processing (step S100). The pupil detection processing at step S100 is the same as the pupil detection processing in the first variation of the first example embodiment. Next, the image processing device 102 performs light source control processing (step S140). As is described later in detail, in a case where the pupil is not detected from the visible image, the image processing device 102 increases the intensity of the near-infrared light emitted by the light source 500 by the light source control processing. Then, the image processing device 102 performs the pupil detection processing again in a state in which the intensity of the near-infrared light is increased. The output unit 190 outputs information on the detected pupil obtained by the pupil detection processing and a face image (step S110). The operation at step S110 is similar to the operation at step S110 in the first variation of the first example embodiment. However, in a case where the pupil detection processing is performed again, the information on the pupil and the face image transmitted at step S110 are the information on the pupil and the face image obtained by the pupil detection processing performed again. Then, the authentication device 400 performs authentication processing (step S120). The authentication processing at step S120 is the same as the operation of the authentication processing at step S120 in the first variation of the first example embodiment.

Figure 14:
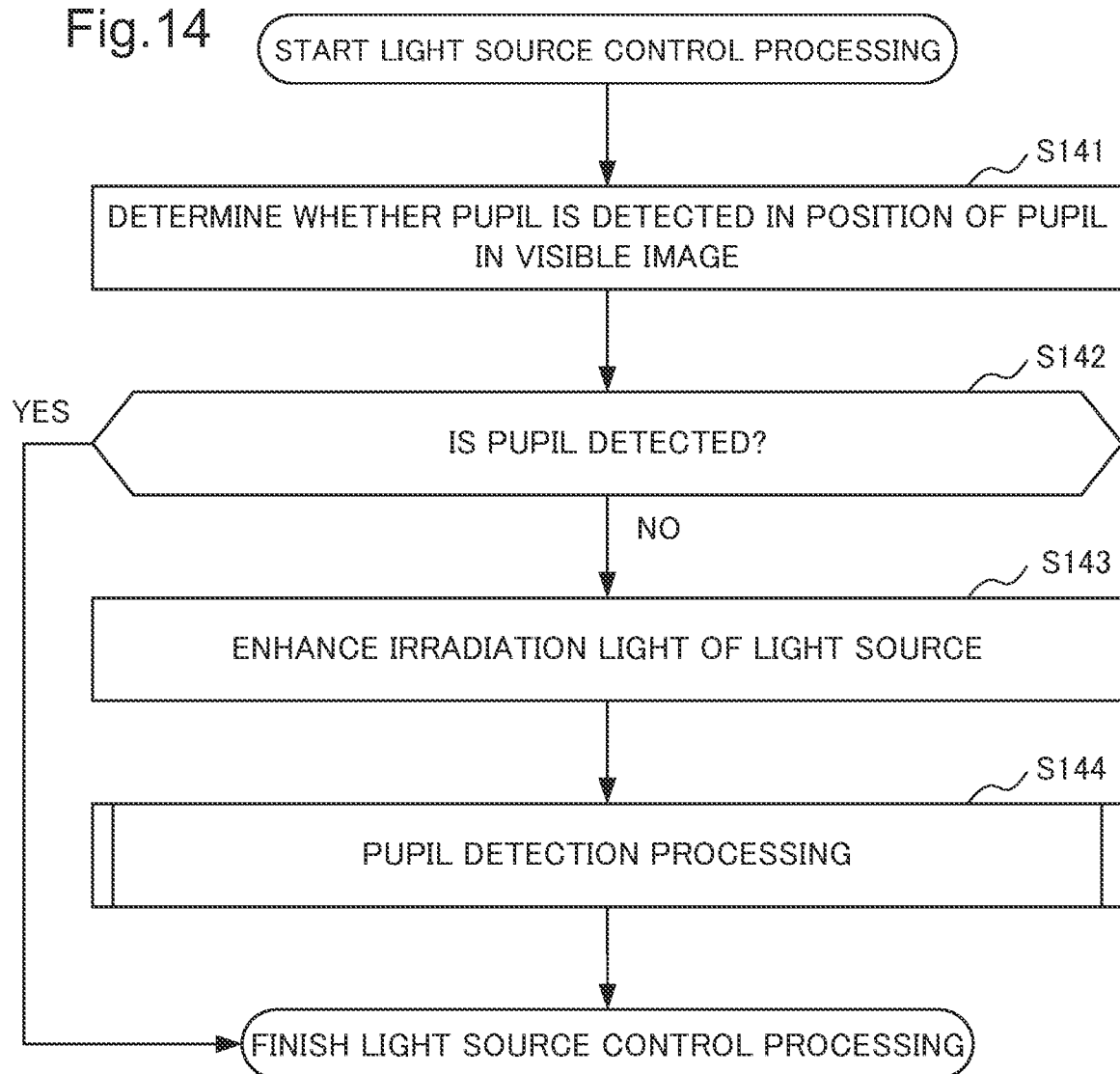
FIG. 14 is a flowchart illustrating an example of an operation of light control processing of the authentication system of the fourth variation of the first example embodiment of the disclosure.

FIG. 14 is a flowchart illustrating an example of the operation of the light source control processing of the authentication system 11 of this variation. In the example of the operation in FIG. 14, first, the third detection unit 180 determines whether the pupil is detected at the position of the pupil in the visible image (step S141). At step S141, the third detection unit 180 may determine whether the pupil is detected from the visible image similarly to the operation at step S132 of the determination unit 181 of the third variation of the first example embodiment. In a case where the pupil is detected from the visible image (YES at step S142), the image processing device 102 finishes the light source control processing. In a case where the pupil is not detected from the visible image (NO at step S142), the light source control unit 182 enhances the irradiation light of the light source 500 (step S143). Then, the image processing device 102 performs the pupil detection processing (step S144). The pupil detection processing at step S144 may be the same as the pupil detection processing at step S100.

For example, in a case where an authentication site is an iris, a person to be imaged wears sunglasses, and absorption of the near-infrared light by the sunglasses is not zero, brightness of a region of the iris in the near-infrared input image decreases. The light source control unit 182 of this variation may improve the brightness of the region of the iris in the near-infrared input image by increasing the intensity of the near-infrared light emitted by the light source 500. If the brightness of the region of the iris is improved and a sharp image of the iris is obtained, accuracy of authentication is improved.

The image processing device 102 may be configured so that the first input unit 110 does not obtain the visible input image and the second input unit 120 obtains the near-infrared input image after the light source control unit 182 increases the intensity of the near-infrared light emitted by the light source 500. In this case, the output unit 190 may be configured to output the information on the pupil detected based on the visible input image and the near-infrared input image obtained first, and the near-infrared input image obtained after the intensity of the emitted near-infrared light increases.

The variations of the first example embodiment described above may be combined in any manner within a possible range.

Second Example Embodiment

Next, a second example embodiment of the disclosure is described in detail with reference to the drawings.

Configuration

Figure 15:
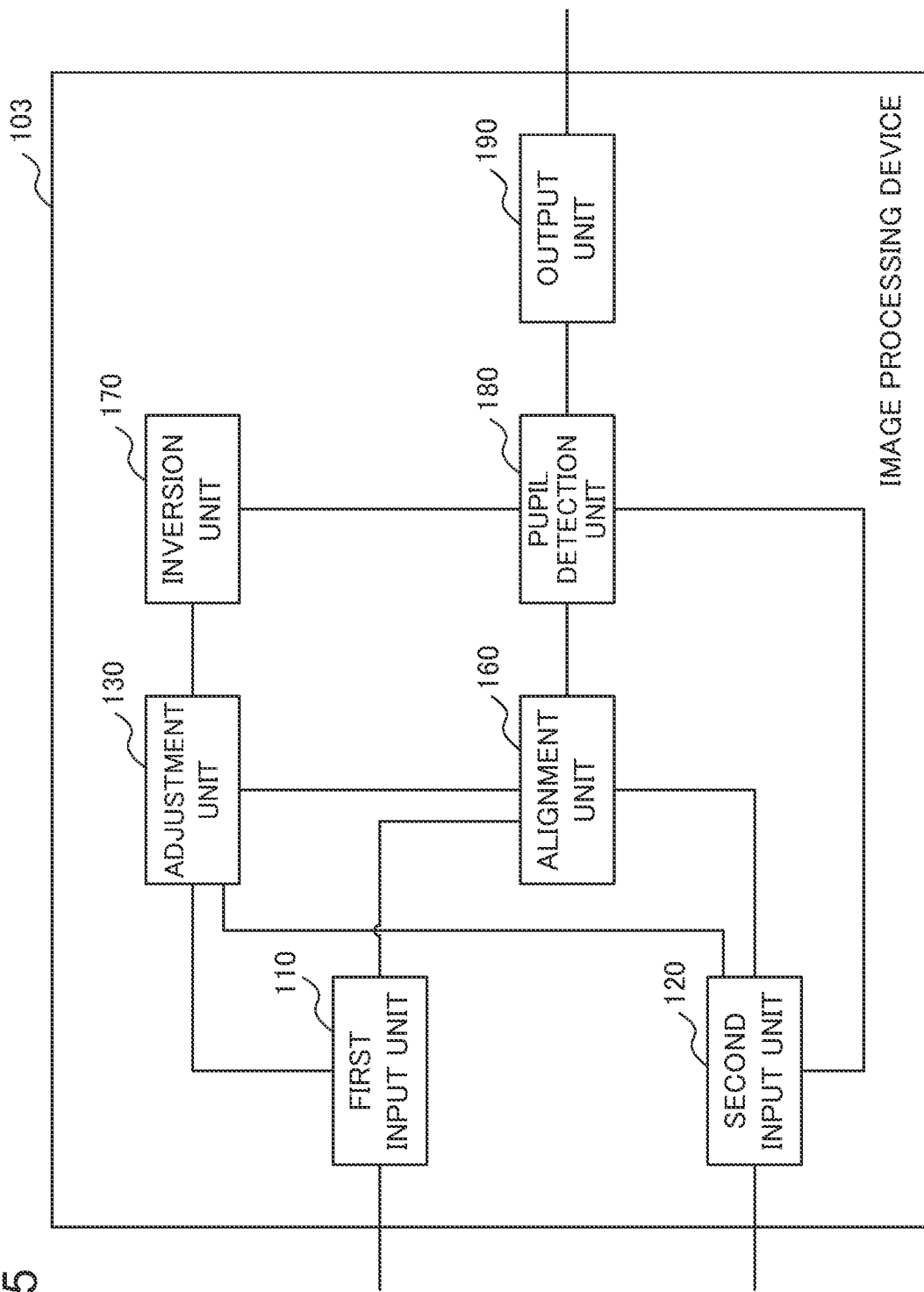
FIG. 15 is a block diagram illustrating an example of a configuration of an image processing device of a second example embodiment of the disclosure.

FIG. 15 is a block diagram illustrating an example of a configuration of an image processing device 103 of the example embodiment. The image processing device 103 an example of the configuration of which is illustrated in FIG. 15 includes a first input unit 110, a second input unit 120, an adjustment unit 130, an alignment unit 160, an inversion unit 170, a pupil detection unit 180, and an output unit 190.

The first input unit 110 receives a visible image of a face. The second input unit 120 receives a near-infrared image of the face. The adjustment unit 130 adjusts brightness of the visible image based on a frequency distribution of pixel values of the visible image and a frequency distribution of pixel values of the near-infrared image. The alignment unit 160 specifies a relative position at which the visible image is related to the near-infrared image. The inversion unit 170 inverts adjusted brightness of the visible image. The pupil detection unit 180 detects a region of a pupil from a synthetic image obtained by adding up the visible image the brightness of which is inverted and the near-infrared image based on the relative position. The output unit 190 outputs information on the detected pupil. The pupil detection unit 180 corresponds to the third detection unit 180 of the first example embodiment.

Operation

Next, an operation of the image processing device 103 of the example embodiment is described in detail with reference to the drawings.

Figure 16:
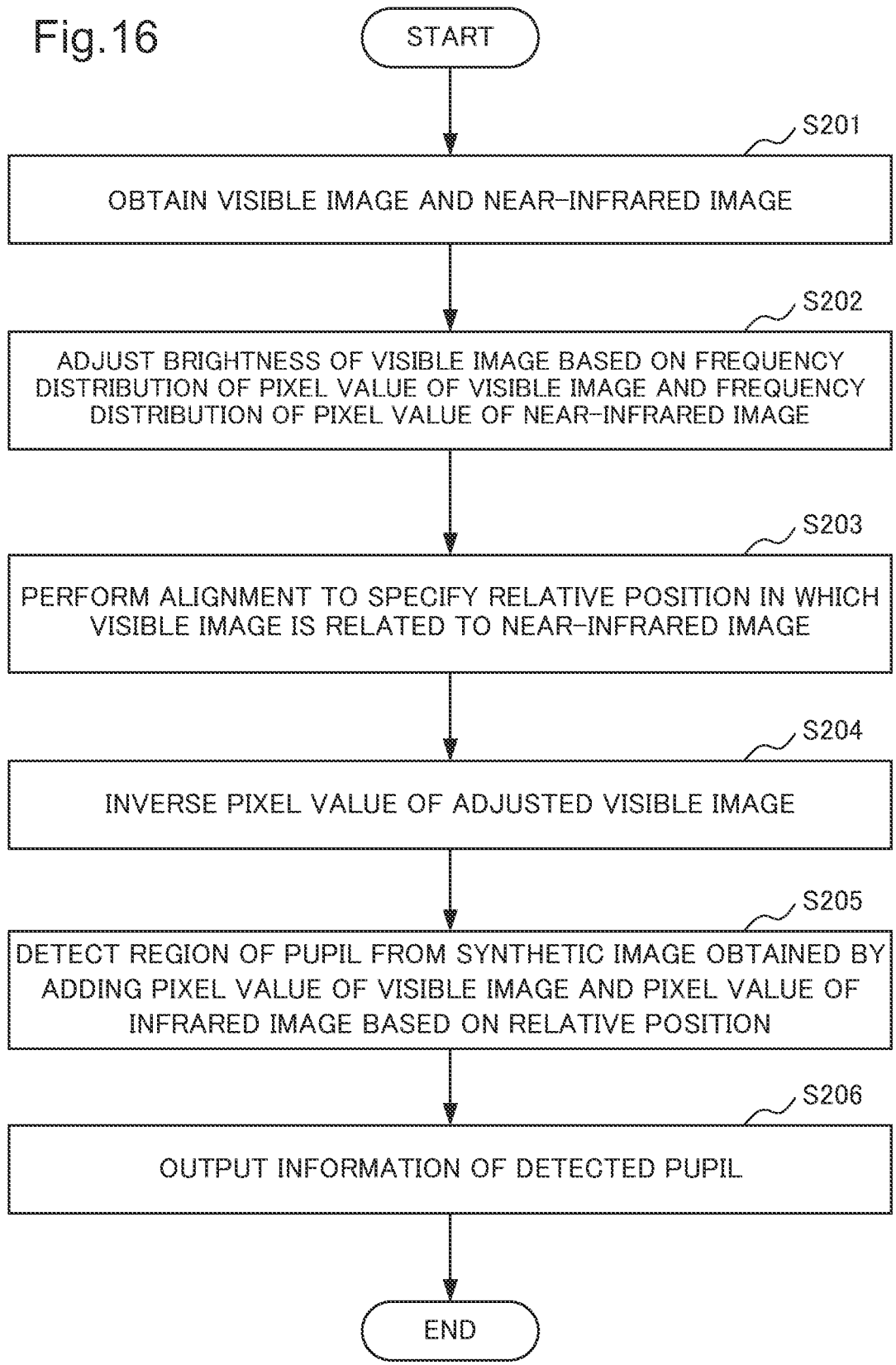
FIG. 16 is a flowchart illustrating an example of an operation the image processing device of the second example embodiment of the disclosure.

FIG. 16 is a flowchart illustrating an example of the operation of the image processing device 103 of the example embodiment. In the example of the operation illustrated in FIG. 16, first, the first input unit 110 obtains the visible image, and the second input unit 120 obtains the near-infrared image (step S201). The visible image corresponds to the visible input image of the first example embodiment. The near-infrared image corresponds to the near-infrared input image of the first example embodiment. Next, the adjustment unit 130 adjusts brightness of the visible image based on the frequency distribution of the pixel values of the visible image and the frequency distribution of the pixel values of the near-infrared image (step S202). The visible image at step S202 corresponds to the visible input image of the first example embodiment. A method of adjusting the brightness of the visible image may be the same as the method of adjusting the brightness of the visible input image by the adjustment unit 130 of the first example embodiment. The adjustment unit 130 may generate an adjusted visible image with adjusted brightness. Next, the alignment unit 160 performs alignment to specify a relative position at which the visible image is related to the near-infrared image (step S203). The visible image at step S203 may be the visible image the brightness of which is adjusted at step S202 (corresponding to the adjusted visible image of the first example embodiment). Next, the inversion unit 170 inverts the pixel value of the adjusted visible image. A method by which the inversion unit 170 inverts the pixel value of the adjusted visible image may be the same as the method by which the inversion unit 170 of the first example embodiment inverts the pixel value of the adjusted visible image. Then, the pupil detection unit 180 detects the region of the pupil from the synthetic image obtained by adding up the pixel values of the visible image and the near-infrared pixel values based on the relative position (step S205). The visible image at step S205 is the adjusted visible image. Then, the output unit 190 outputs the information on the detected pupil (step S206). The information on the pupil may be the same as the information on the pupil output by the output unit 190 of the first example embodiment.

Effect

The example embodiment has an effect of reducing a cost for detecting the pupil. A reason for this is the same as the reason that the effect of reducing the cost for detecting the pupil is obtained in the first example embodiment.

Another Example Embodiment

Each of the image processing device and the authentication device according to the above-described example embodiments of the disclosure may be implemented by a computer including a memory into which a program read from a storage medium is loaded and a processor that executes the program. The computer may be implemented by a plurality of communicably connected computers. Each of the image processing device and the authentication device according to the above-described example embodiments may also be implemented by dedicated hardware such as a circuit, for example. Each of the image processing device and the authentication device according to the above-described example embodiments may also be implemented by a combination of the above-described computer and dedicated hardware.

Figure 17:
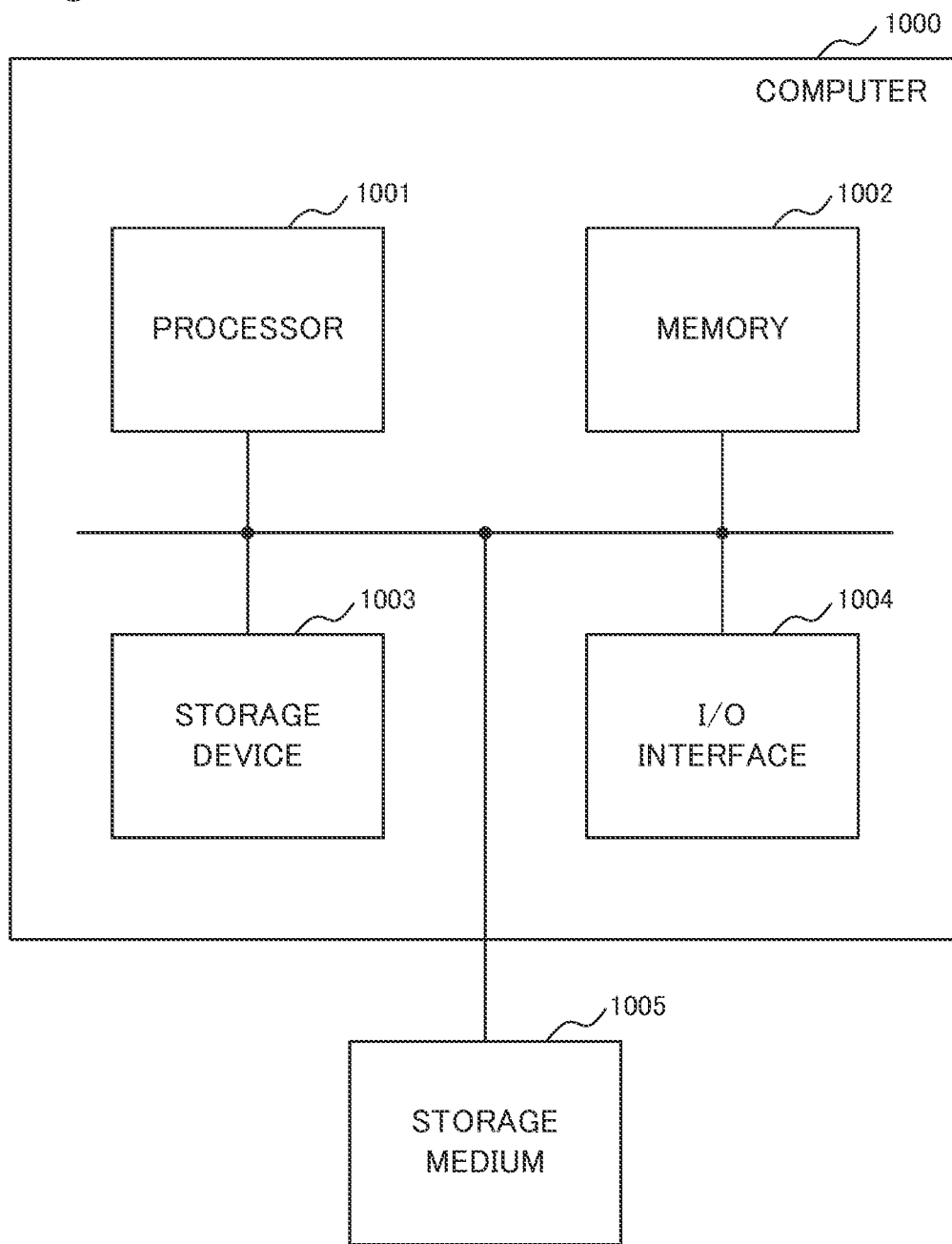
FIG. 17 is a block diagram illustrating an example of a configuration of a computer capable of implementing the image processing device and the authentication device according to the example embodiments of the disclosure.

FIG. 17 is a view illustrating an example of a hardware configuration of a computer 1000 that may implement the image processing device and the authentication device according to the above-described example embodiments. In the example illustrated in FIG. 17, the computer 1000 includes a processor 1001, a memory 1002, a storage device 1003, and an input/output (I/O) interface 1004. The computer 1000 may access a storage medium 1005. The memory 1002 and the storage device 1003 are, for example, storage devices such as a random access memory (RAM) and a hard disk. The storage medium 1005 is, for example, a storage device such as a RAM and a hard disk, a read only memory (ROM), or a portable storage medium. The storage device 1003 may be the storage medium 1005. The processor 1001 may read/write data and programs from/in the memory 1002 and the storage device 1003. The processor 1001 may access, for example, other devices via the I/O interface 1004. The processor 1001 may access the storage medium 1005. The storage medium 1005 stores any of programs for operating the computer 1000 as the image processing device and the authentication device according to the above-described example embodiments.

The processor 1001 loads the program, stored in the storage medium 1005, that causes the computer 1000 to operate as the device (that is, either the image processing device or the authentication device) according to the above-described example embodiments into the memory 1002. Then, the processor 1001 executes the program loaded into the memory 1002, so that the computer 1000 operates as the above-described device.

The first input unit 110, the second input unit 120, the adjustment unit 130, the first detection unit 140, the second detection unit 150, the alignment unit 160, the inversion unit 170, the third detection unit 180, and the output unit 190 may be implemented by the processor 1001 that executes the program loaded into the memory 1002. The determination unit 181 and the light source control unit 182 may also be implemented by the processor 1001 that executes the program loaded into the memory 1002. The pupil detection unit 180 may also be implemented by the processor 1001 that executes the program loaded into the memory 1002.

A part or all of the first input unit 110, the second input unit 120, the adjustment unit 130, the first detection unit 140, the second detection unit 150, the alignment unit 160, the inversion unit 170, the third detection unit 180, and the output unit 190 may be implemented by a dedicated circuit. A part or all of the determination unit 181, the light source control unit 182, and the pupil detection unit 180 may also be implemented by a dedicated circuit.

A part or all of the above-described example embodiments may be described as in the following supplementary notes, but are not limited to the following.

(Supplementary Note 1)

An image processing device including:
 first input means for receiving a visible image of a face;
 second input means for receiving a near-infrared image of the face;
 adjustment means for adjusting brightness of the visible image based on a frequency distribution of pixel values of the visible image and a frequency distribution of pixel values of the near-infrared image;
 alignment means for specifying a relative position at which the visible image is related to the near-infrared image;
 inversion means for inverting adjusted brightness of the visible image;
 pupil detection means for detecting a region of a pupil from a synthetic image obtained by adding up the visible image the brightness of which is inverted and the near-infrared image based on the relative position; and
 output means for outputting information on the detected pupil.

(Supplementary Note 2)

The image processing device according to supplementary note 1, including:
 first detection means for detecting a face from the visible image; and
 second detection means for detecting a face from the near-infrared image, wherein
 the pupil detection means detects the region of the pupil in a case where the face is detected from both the visible image and the near-infrared image.

(Supplementary Note 3)

The image processing device according to supplementary note 1 or 2, wherein
 the adjustment means adjusts the pixel values of the visible image in such a way that a distribution of the pixel values of the visible image approaches a distribution of the pixel values of the near-infrared image.

(Supplementary Note 4)

The image processing device according to any one of supplementary notes 1 to 3, wherein
 the adjustment means adjusts the pixel values of the visible image in such a way that at least a part of a shape of the frequency distribution of the visible image approaches a shape of the frequency distribution of the near-infrared image in a range of the pixel values excluding a first range including a darkest pixel value and a second range including a brightest pixel value of the near-infrared image.

(Supplementary Note 5)

The image processing device according to supplementary note 4, wherein
 the adjustment means adjusts the pixel values of the visible image in such a way that a pixel value indicated by a frequency peak in a first range from the darkest pixel value in the frequency distribution of the visible image coincides with a pixel value indicating a frequency peak in a second range from the darkest pixel value in the frequency distribution of the near-infrared image.

(Supplementary Note 6)

The image processing device according to any one of supplementary notes 1 to 5, including:
 determination means for determining wearing of sunglasses based on the pixel values of the pixels in a region including the region of the pupil in the visible image.

(Supplementary Note 7)

The image processing device according to any one of supplementary notes 1 to 6, including:
 light source control means for controlling intensity of light of a light source that irradiates the face with light based on the pixel values of the pixels in the region including the region of the pupil.

(Supplementary Note 8)

An image processing system including the image processing device according to any one of supplementary notes 1 to 7, further including:
 visible imaging device that captures the visible image; and
 near-infrared imaging device that captures the near-infrared image.

(Supplementary Note 9)

An image processing method including:
 receiving a visible image of a face;
 receiving a near-infrared image of the face;
 adjusting brightness of the visible image based on a frequency distribution of pixel values of the visible image and a frequency distribution of pixel values of the near-infrared image;
 alignment means for specifying a relative position at which the visible image is related to the near-infrared image;
 inverting adjusted brightness of the visible image;
 detecting a region of a pupil from a synthetic image obtained by adding up the visible image the brightness of which is inverted and the near-infrared image based on the relative position; and
 outputting information on the detected pupil.

(Supplementary Note 10)

The image processing method according to supplementary note 9, including:

detecting a face from the visible image;

detecting a face from the near-infrared image; and detecting the region of the pupil in a case where the face is detected from both the visible image and the near-infrared image.

(Supplementary Note 11)

The image processing method according to supplementary note 9 or 10, including:

adjusting the pixel values of the visible image in such a way that a distribution of the pixel values of the visible image approaches a distribution of the pixel values of the near-infrared image.

(Supplementary Note 12)

The image processing method according to any one of supplementary notes 9 to 11, including:

adjusting the pixel values of the visible image in such a way that at least a part of a shape of the frequency distribution of the visible image approaches a shape of the frequency distribution of the near-infrared image in a range of the pixel values excluding a first range including a darkest pixel value and a second range including a brightest pixel value of the near-infrared image.

(Supplementary Note 13)

The image processing method according to supplementary note 12, including:

adjusting the pixel values of the visible image in such a way that a pixel value indicated by a frequency peak in a first range from the darkest pixel value in the frequency distribution of the visible image coincides with a pixel value indicating a frequency peak in a second range from the darkest pixel value in the frequency distribution of the near-infrared image.

(Supplementary Note 14)

The image processing method according to any one of supplementary notes 9 to 13, including:

determining wearing of sunglasses based on the pixel values of the pixels in a region including the region of the pupil in the visible image.

(Supplementary Note 15)

The image processing method according to any one of supplementary notes 9 to 14, including:

controlling intensity of light of a light source that irradiates the face with light based on the pixel values of the pixels in the region including the region of the pupil.

(Supplementary Note 16)

A storage medium storing a program that causes a computer to execute:

first input processing of receiving a visible image of a face;

second input processing for receiving a near-infrared image of the face;

adjustment processing of adjusting brightness of the visible image based on a frequency distribution of pixel values of the visible image and a frequency distribution of pixel values of the near-infrared image;

alignment processing of specifying a relative position at which the visible image is related to the near-infrared image;

inversion processing of inverting adjusted brightness of the visible image;

pupil detection processing of detecting a region of a pupil from a synthetic image obtained by adding up the visible image the brightness of which is inverted and the near-infrared image based on the relative position; and output processing of outputting information on the detected pupil.

(Supplementary Note 17)

The storage medium according to supplementary note 16, wherein the program causes the computer to further execute:

first detection processing of detecting a face from the visible image; and second detection processing of detecting a face from the near-infrared image, and the pupil detection processing detects the region of the pupil in a case where the face is detected from both the visible image and the near-infrared image.

(Supplementary Note 18)

The storage medium according to supplementary note 16 or 17, wherein the adjustment processing adjusts the pixel values of the visible image in such a way that a distribution of the pixel values of the visible image approaches a distribution of the pixel values of the near-infrared image.

(Supplementary Note 19)

The storage medium according to any one of supplementary notes 16 to 18, wherein the adjustment processing adjusts the pixel values of the visible image in such a way that at least a part of a shape of the frequency distribution of the visible image approaches a shape of the frequency distribution of the near-infrared image in a range of the pixel values excluding a first range including a darkest pixel value and a second range including a brightest pixel value of the near-infrared image.

(Supplementary Note 20)

The storage medium according to supplementary note 19, wherein the adjustment processing adjusts the pixel values of the visible image in such a way that a pixel value indicated by a frequency peak in a first range from the darkest pixel value in the frequency distribution of the visible image coincides with a pixel value indicating a frequency peak in a second range from the darkest pixel value in the frequency distribution of the near-infrared image.

(Supplementary Note 21)

The storage medium according to any one of supplementary notes 16 to 20, wherein the program causes the computer to further execute:

determination processing of determining wearing of sunglasses based on the pixel values of the pixels in a region including the region of the pupil in the visible image.

(Supplementary Note 22)

The storage medium according to any one of supplementary notes 16 to 21, wherein the program causes the computer to further execute:

light source control processing of controlling intensity of light of a light source that irradiates the face with light based on the pixel values of the pixels in the region including the region of the pupil.

Although the disclosure has been particularly shown and described with reference to the example embodiments thereof, the disclosure is not limited to these example embodiments. It will be understood by those of ordinary skill in the art that various changes in form and details may be made therein without departing from the spirit and scope of the disclosure as defined by the claims.

REFERENCE SIGNS LIST 1 image processing system
2 image processing system
10 authentication system
11 authentication system
100 image processing device
101 image processing device
102 image processing device
103 image processing device
110 first input unit
120 second input unit
130 adjustment unit
140 first detection unit
150 second detection unit
160 alignment unit
170 inversion unit
180 third detection unit
180 pupil detection unit
181 determination unit
182 light source control unit
190 output unit
200 visible imaging device
300 near-infrared imaging device
400 authentication device
410 authentication unit
420 second output unit
500 light source
1000 computer
1001 processor
1002 memory
1003 storage device
1004 I/O interface
1005 storage medium

The invention claimed is:

1. An image processing device comprising:
at least one memory storing instructions; and
at least one processor configured to execute the instructions to:
receive a visible image of a face;
receive a near-infrared image of the face;
adjust brightness of the visible image based on a frequency distribution of pixel values of the visible image and a frequency distribution of pixel values of the near-infrared image;
specify a relative position at which the visible image is related to the near-infrared image;
invert the adjusted brightness of the visible image;
detect a region of a pupil within a synthetic image obtained by adding up the visible image in which the brightness has been inverted and adjusted and the near-infrared image based on the relative position;
determine whether a visible pupil region is detected within the visible image at a position corresponding to the region of the pupil detected within the synthetic image;
in response to determining that the visible pupil region has not been detected within the visible image at the position, controlling a light source to increase intensity of emitted near-infrared light, and again receive the near-infrared image;
perform a determination of presence of sunglasses based on a pixel value of a pixel included in the visible pupil region detected within the visible image, the visible pupil area corresponding to the detected region of the pupil detected within the synthetic image; and
output a result of the determination.

2. The image processing device according to claim 1, wherein
the at least one processor is configured to execute the instructions to further:
extract a new iris region within the new near-infrared image; and
perform iris authentication using the extracted new iris region.

3. The image processing device according to claim 1, wherein
the at least one processor is configured to execute the instructions to further:
detect a face within the visible image;
detect a face within the near-infrared image; and
detect the region of the pupil within the synthetic image in response to the face having been detected within both the visible image and the near-infrared image.

4. The image processing device according to claim 1, wherein
the at least one processor is configured to execute the instructions to further:
adjust the pixel values of the visible image such that a distribution of the pixel values of the visible image approaches a distribution of the pixel values of the near-infrared image.

5. The image processing device according to claim 1, wherein
the at least one processor is configured to execute the instructions to further:
adjust the pixel values of the visible image such that at least a part of a shape of the frequency distribution of the visible image approaches a shape of the frequency distribution of the near-infrared image in a range of the pixel values excluding a first range including a darkest pixel value and a second range including a brightest pixel value of the near-infrared image.

6. The image processing device according to claim 3, wherein
the at least one processor is configured to execute the instructions to further:
adjust the pixel values of the visible image such that a pixel value indicated by a frequency peak in a first range from the darkest pixel value in the frequency distribution of the visible image coincides with a pixel value indicating a frequency peak in a second range from the darkest pixel value in the frequency distribution of the near-infrared image.

7. An image processing system including the image processing device according to claim 1, comprising:
a visible imaging device that captures the visible image; and
a near-infrared imaging device that captures the near-infrared image.

8. An image processing method comprising:
receiving, by a processor, a visible image of a face;
receiving, by the processor, a near-infrared image of the face;
adjusting, by the processor, brightness of the visible image based on a frequency distribution of pixel values of the visible image and a frequency distribution of pixel values of the near-infrared image;
specifying, by the processor, a relative position at which the visible image is related to the near-infrared image;
inverting, by the processor, the adjusted brightness of the visible image;
detecting, by the processor, a region of a pupil within a synthetic image obtained by adding up the visible image in which the brightness has been inverted and adjusted and the near-infrared image based on the relative position;

determining, by the processor, whether a visible pupil region is detected within the visible image at a position corresponding to the region of the pupil detected within the synthetic image;

in response to determining that the visible pupil region has not been detected within the visible image at the position, controlling, by the processor, a light source to increase intensity of emitted near-infrared light, and again receive the near-infrared image;

performing, by the processor, a determination of presence of sunglasses based on a pixel value of a pixel included in the visible pupil region detected within the visible image, the visible pupil area corresponding to the detected region of the pupil detected within the synthetic image; and outputting, by the processor, a result of the determination.

9. The image processing method according to claim 8, further comprising:

extracting, by a processor, a new iris region within the new near-infrared image; and performing, by the processor, iris authentication using the extracted new iris region.

10. The image processing method according to claim 8, further comprising:

detecting, by the processor, a face within the visible image;

detecting, by the processor, a face within the near-infrared image; and detecting, by the processor, the region of the pupil within the synthetic image in response to the face having been detected within both the visible image and the near-infrared image.

11. The image processing method according to claim 8, further comprising:

adjusting, by the processor, the pixel values of the visible image such that a distribution of the pixel values of the visible image approaches a distribution of the pixel values of the near-infrared image.

12. The image processing method according to claim 8, further comprising:

adjusting, by the processor, the pixel values of the visible image such that at least a part of a shape of the frequency distribution of the visible image approaches a shape of the frequency distribution of the near-infrared image in a range of the pixel values excluding a first range including a darkest pixel value and a second range including a brightest pixel value of the near-infrared image.

13. The image processing method according to claim 10, further comprising:

adjusting, by the processor, the pixel values of the visible image such that a pixel value indicated by a frequency peak in a first range from the darkest pixel value in the frequency distribution of the visible image coincides with a pixel value indicating a frequency peak in a second range from the darkest pixel value in the frequency distribution of the near-infrared image.

14. The image processing method according to claim 8, further comprising:

capturing the visible image by a visible imaging device; and capturing the near-infrared image by a near-infrared imaging device.

15. A non-transitory computer readable storage medium storing a program executable by a computer to cause the computer to perform processing of:

receiving a visible image of a face;

receiving a near-infrared image of the face;

adjusting brightness of the visible image based on a frequency distribution of pixel values of the visible image and a frequency distribution of pixel values of the near-infrared image;

specifying a relative position at which the visible image is related to the near-infrared image;

inverting the adjusted brightness of the visible image;

detecting a region of a pupil within a synthetic image obtained by adding up the visible image in which the brightness has been inverted and adjusted and the near-infrared image based on the relative position;

determining whether a visible pupil region is detected within the visible image at a position corresponding to the region of the pupil detected within the synthetic image;

in response to determining that the visible pupil region has not been detected within the visible image at the position, controlling a light source to increase intensity of emitted near-infrared light, and again receive the near-infrared image;

performing a determination of presence of sunglasses based on a pixel value of a pixel included in the visible pupil region detected within the visible image, the visible pupil area corresponding to the detected region of the pupil detected within the synthetic image; and outputting a result of the determination.

16. The storage medium according to claim 15, wherein the program is executable by the computer to cause the computer to execute further processing of:

extracting a new iris region within the new near-infrared image; and performing iris authentication using the extracted new iris region.

17. The storage medium according to claim 15, wherein the program is executable by the computer to cause the computer to execute further processing of:

detecting a face within the visible image;

detecting a face within the near-infrared image; and detecting the region of the pupil within the synthetic image in response to the face having been detected within both the visible image and the near-infrared image.

* * * * *